(12) United States Patent
Failli et al.

(10) Patent No.: US 6,903,087 B2
(45) Date of Patent: Jun. 7, 2005

(54) PYRIDO CYCLOHEXENYL PHENYL CARBOXAMIDES TOCOLYTIC OXYTOCIN RECEPTOR ANTAGONISTS

(75) Inventors: Amedeo Arturo Failli, Princeton Junction, NJ (US); William Jennings Sanders, Fox Lake, IL (US); Eugene John Trybulski, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 60 days.

(21) Appl. No.: 10/119,894

(22) Filed: Apr. 10, 2002

(65) Prior Publication Data

US 2003/0055046 A1 Mar. 20, 2003

Related U.S. Application Data

(60) Provisional application No. 60/283,388, filed on Apr. 12, 2001.

(51) Int. Cl.$^7$ .................. A61K 31/33; A61K 31/55; C07D 487/12
(52) U.S. Cl. .................. 514/183; 514/220; 540/561
(58) Field of Search .................. 514/183, 220; 540/561

(56) References Cited

U.S. PATENT DOCUMENTS

| | | | |
|---|---|---|---|
| 5,736,540 A | 4/1998 | Albright et al. | 514/220 |
| 5,880,122 A * | 3/1999 | Trybulski et al. | 514/220 |
| 5,968,930 A | 10/1999 | Albright et al. | 514/220 |
| 2002/0183311 A1 | 12/2002 | Failli et al. | 514/220 |
| 2002/0198196 A1 | 12/2002 | Failli et al. | 514/220 |
| 2003/0004159 A1 | 1/2003 | Failli et al. | 514/220 |
| 2003/0008863 A1 | 1/2003 | Failli et al. | 514/220 |
| 2003/0018026 A1 | 1/2003 | Failli et al. | 514/220 |
| 2003/0027815 A1 | 2/2003 | Failli et al. | 514/220 |
| 2003/0055047 A1 | 3/2003 | Failli et al. | 514/220 |

FOREIGN PATENT DOCUMENTS

| | | |
|---|---|---|
| WO | 98/20011 | 5/1998 |
| WO | 99/06409 | 2/1999 |

OTHER PUBLICATIONS

Banker, G. S. et al., "Modern Pharmaceutics, 3ed.", Marcel Dekker, New York, 1996, p. 596.

Wolff, Manfred E., "Burger's Medicinal Chemistry, 5ed, Part 1", John Wiley & Sons, 1995, pp. 975–977.

* cited by examiner

Primary Examiner—Mukund J. Shah
Assistant Examiner—Sudhaker B. Patel
(74) Attorney, Agent, or Firm—Woodcock Washburn LLP

(57) ABSTRACT

The present invention provides novel tricyclic pyridyl carboxamides as well as methods and pharmaceutical compositions utilizing them compounds for the treatment and/or prevention and/or suppression of disorders which may be remedied or alleviated by oxytocin antagonist activity, including prevention and/or suppression of preterm labor, suppression of labor at term prior to caesarean delivery, and for the treatment of dysmenorrhea. These compounds are also useful in enhancing fertility rates, enhancing survival rates and synchronizing estrus in farm animals; and may be useful in the prevention and treatment of disfunctions of the oxytocin system in the central nervous system including obsessive compulsive disorder (OCD) and neuropsychiatric disorders.

15 Claims, No Drawings

PYRIDO CYCLOHEXENYL PHENYL CARBOXAMIDES TOCOLYTIC OXYTOCIN RECEPTOR ANTAGONISTS

This application claims priority from copending provisional application Serial No. 60/283,388, filed Apr. 12, 2001, the entire disclosure of which is hereby incorporated by reference.

This invention concerns novel tricyclic pyridyl carboxamides which act as competitive oxytocin receptor antagonists, as well as methods of their manufacture, methods of treatment and pharmaceutical compositions utilizing these compounds. The compounds of the present invention are useful therapeutic agents in mammals, particularly in humans. More specifically, they can be used in the prevention and/or suppression of preterm labor, for the suppression of labor at term prior to caesarean delivery, to facilitate antinatal transport to a medical facility, and for the treatment of dysmenorrhea.

These compounds also useful in enhancing fertility rates, enhancing survival rates and synchronizing estrus in farm animals; and may be useful in the prevention and treatment of disfunctions of the oxytocin system in the central nervous system including obsessive compulsive disorder (OCD) and neuropsychiatric disorders.

BACKGROUND OF THE INVENTION

Premature labor remains the leading cause of perinatal mortality and morbidity. Infant mortality dramatically decreases with increased gestational age. The survival rate of prematurely born infants increases from 20% at 24 weeks to 94% at 30 weeks. Moreover the cost associated with the care of an infant born prematurely is very high. While many agents have been developed for the treatment of premature labor in the last 40 years, the incidence of pre-term births and low birth weight infants has remained relatively unchanged. Therefore there remains an unmet need for the development of a safe and effective treatment of preterm labor.

Tocolytic (uterine relaxing) agents currently in use include $\beta_2$ adrenergic receptor agonists such as Ritodrine which is moderately effective in suppressing preterm labor, but it is associated with maternal hypotension, tachycardia, and metabolic side effects. Several other agents have been used to suppress premature labor, including other $\beta_2$ adrenergic agonists (terbutaline, albuterol), magnesium sulfate, NSAIDs (indomethacin), and calcium channel blockers. The consensus is that none of these agents is very effective; there is no clinical evidence showing that these compounds can prolong gestation for more than 7 days (Johnson, *Drugs*, 45, 684–692 (1993)). Furthermore, their safety profile is not ideal. Adverse effects include respiratory depression and cardiac arrest (magnesium sulfate), hemodynamic effects (calcium channel blockers), premature closure of the ductus arteriosus and oligohydramnios (NSAIDs; prostaglandin synthase inhibitors). Therefore there is an unmet need for safer and more efficacious agents for the treatment of preterm labor with better patient tolerability. Specific requirements with regard to safety include a product with no or low rates of tachycardia, limited anxiety, improved fetal safety, and few, if any, adverse cardiovascular effects.

One target of interest is the oxytocin receptor in the uterus, and a selective oxytocin receptor antagonist has been proposed as an ideal tocolytic agent. While the exact role of oxytocin (OT) in parturition has not been clearly defined, there is evidence strongly suggesting that it may play a critical role in the initiation and progression of labor in humans (Fuchs et al. *Science* 215, 1396–1398 (1982); Maggi et al. *J. Clin. Endocrinol. Metab.* 70, 1142–1154 (1990); Åkerlund, *Reg. Pept.* 45, 187–191 (1993); Åkerlund, Int. Congr. Symp. Semin. Ser., *Progress in Endocrinology* 3, 657–660 (1993); Åkerlund et al., in *Oxytocin*, Ed. R. Ivell and J. Russel, Plenum Press, New York, pp 595–600 (1995)). Preliminary clinical trials with oxytocin receptor antagonists support the concept that a blockade of OT receptors reduces uterine myometrial activity and delays the onset of labor (Åkerlund et al., *Br. J. Obst. Gynaecol.* 94, 1040–1044, (1987); Andersen et al., *Am. J. Perinatol.* 6, 196–199 (1989); Melin, *Reg. Pept.* 45, 285–288 (1993)). Thus, a selective oxytocin antagonist is expected to block the major effects of oxytocin exerted mainly on the uterus at term, and to be more efficacious than current therapies for the treatment of preterm labor. By virtue of its direct action on the receptors in the uterus an oxytocin antagonist is also expected to have fewer side effects and an improved safety profile.

The following references describe peptidic oxytocin antagonists: Hruby et al., Structure-Activity Relationships of Neurohypophyseal Peptides, in *The Peptides: Analysis, Synthesis and Biology*; Udenfriend and Meienhofer Eds., Academic Press, New York, Vol. 8, 77–207 (1987); Pettibone et al., *Endocrinology*, 125, 217 (1989); Manning et al., Synthesis and Some Uses of Receptor-Specific Agonists and Antagonists of Vasopressin and Oxytocin, *J. Recept. Res.*, 13, 195–214 (1993); Goodwin et al., Dose Ranging Study of the Oxytocin Antagonist Atosiban in the Treatment of Preterm Labor, *Obstet. Gynecol.*, 88, 331–336 (1996). Peptidic oxytocin antagonists suffer from a lack of oral activity and many of these peptides are non-selective antagonists since they also exhibit vasopressin antagonist activity. Bock et al. [*J. Med. Chem.* 33, 2321 (1990)], Pettibone et al. [*J. Pharm. Exp. Ther.* 256, 304 (1991)], and Williams et al. [J. Med. Chem., 35, 3905 (1992)] have reported on potent hexapeptide oxytocin antagonists which also exhibit weak vasopressin antagonistic activity in binding to $V_1$ and $V_2$ receptors.

Various non-peptidic oxytocin antagonists and/or oxytocin/vasopressin (AVP) antagonists have recently been reported by Pettibone et al., *Endocrinology*, 125, 217 (1989); Yamamura et al., *Science*, 252, 572–574 (1991); Evans et al., *J. Med. Chem.*, 35, 3919–3927 (1992); Pettibone et al., *J. Pharmacol. Exp. Ther*, 264, 308–314 (1992); Ohnishi et al., *J. Clin. Pharmacol.* 33, 230–238, (1993); Evans et al., *J. Med. Chem.* 36, 3993–4006 (1993); Pettibone et al., *Drug Dev. Res.* 30, 129–142 (1993); Freidinger et al., General Strategies in Peptidomimetic Design: Applications to Oxytocin Antagonists, in *Perspect. Med. Chem.* 179–193 (1993), Ed. B. Testa, Verlag, Basel, Switzerland; Serradeil-LeGal, *J. Clin. Invest.*, 92, 224–231 (1993); Williams et al., *J. Med. Chem.* 37, 565–571 (1994); Williams et al., *Bioorg. Med. Chem.* 2, 971–985 (1994); Yamamura et al., *Br. J. Pharmacol.*, 105, 546–551 (1995); Pettibone et al., *Advances in Experimental Medicine and Biology* 395, 601–612 (1995); Williams et al., *J. Med. Chem.* 38, 4634–4636 (1995); Hobbs et al., *Biorg. Med. Chem. Lett.* 5, 119 (1995); Williams et al., *Curr. Pharm. Des.* 2, 41–58 (1996); Freidinger et al., *Medicinal Research Reviews*, 17, 1–16 (1997); Pettibone et al., *Biochem. Soc. Trans.* 25 (3), 1051–1057 (1997); Bell et al., *J. Med. Chem.* 41, 2146–2163 (1998); Kuo et al., *Bioorg. Med. Chem. Lett.* 8, 3081–3086 (1998); Williams et al., *Biorg. Med. Chem. Lett.* 9, 1311–1316 (1999).

Certain carbostyril derivatives and bicyclic azepines are disclosed as oxytocin and vasopressin antagonists by Ogawa et al. in WO 94/01113 (1994); benzoxazinones are disclosed as oxytocin and vasopressin receptor antagonists by Sparks et al. in WO 97/25992 (1997); Williams et al. disclose piperidine oxytocin and vasopressin receptor antagonists in WO 96/22775 (1996); Bock et al. disclose benzoxazinone and benzopyrimidinone piperidines useful as oxytocin and vasopressin receptor antagonists in U.S. Pat. No. 5,665,719 (1997); piperazines and spiropiperidines useful as oxytocin and vasopressin receptor antagonists are disclosed by Evans et al. in U.S. Pat. No. 5,670,509 (1997) and by Bock et al. in U.S. Pat. No. 5,756,504 (1998); Bell et al. disclose piperazine oxytocin receptor antagonists in UK Patent Application, GB 2 326 639 A (1998); Bell et al. disclose benzoxazinone and quinolinone oxytocin and vasopressin receptor antagonists in UK Patent Application GB 2 326 410 A (1998); Bell et al. disclose benzoxazinone oxytocin and vasopressin receptor antagonists in U.S. Pat. No. 5,756,497 (1998); Matsuhisa et al. disclose difluoro tetrahydrobenzazepine derivatives as oxytocin antagonists in WO 98/39325 (1998); (1998); Ogawa et al. disclose heterocyclic bisamides with vasopressin and oxytocin antagonist activity in U.S. Pat. No. 5,753,644 (1998); and Ogawa et al. disclose benzazepine derivatives with anti-vasopressin activity, oxytocin antagonistic activity and vasopressin agonist activity, useful as vasopressin antagonists, vasopressin agonists and oxytocin antagonists in WO 97/22591 (1997) and U.S. Pat. No. 6,096,736 (2000).

Trybulski et al. disclose 3-carboxamide derivatives of pyrrolobenzodiazepine bisamides with vasopressin antagonist activity in U.S. Pat. No. 5,880,122 (1999); bicyclic thienoazepines with vasopressin and oxytocin receptor antagonist activity are disclosed by Albright et al. in WO 96/22294 (1996) and U.S. Pat. No. 5,654,297 (1997); and tricyclic benzazepines with vasopressin and oxytocin receptor antagonist activity are disclosed by Albright et al. in WO 96/22282 (1996) and U.S. Pat. No. 5,849,735 (1998).

Albright et al. broadly disclose tricyclic benzazepine compounds which possess antagonistic activity at the $V_1$ and/or $V_2$ receptors and exhibit in vivo vasopressin antagonistic activity, as well as antagonistic activity at the oxytocin receptors.

Venkatesan et al. broadly disclose tricyclic benzazepines with vasopressin and oxytocin antagonist activity in U.S. Pat. No. 5,521,173 (1996), WO 96/22292 (1996), and in U.S. Pat. No. 5,780,471 (1998).

Oxytocin antagonists can be useful for the treatment and/or prevention and/or suppression of preterm labor, for the suppression of term labor prior to a caesarian delivery, and to facilitate antinatal transport to a medical facility. They also can produce contraception in mammals given that oxytocin antagonists have been shown to inhibit the release of oxytocin-stimulated luteneizing hormone (LH) from pituitary cells (Rettori et al., *Proc. Nat Acad. Sci. U.S.A.* 94, 2741–2744 (1997); Evans et al., *J. Endocrinol.*, 122, 107–116 (1989); Robinson et al., *J. Endocrinol.* 125, 425–432 (1990)).

Oxytocin antagonists also have the ability to relax uterine contractions induced by oxytocin in mammals and thus can be also useful for the treatment of dysmenorrhea, a condition characterized by pain during menstruation (Åkerlund, Int. Congr. Symp. Semin. Ser., *Progress in Endocrinology* 3, 657–660 (1993); Åkerlund, *Reg. Pept.* 45, 187–191 (1993); Melin, *Reg. Pept.* 45, 285–288 (1993)). Primary dysmenorrhea is associated with ovulatory cycles, and it is the most common complaint of gynecologic patients. Myometrial hypercontractility and decreased blood flow to the uterus are thought to be causative factors for the symptoms of primary dysmenorrhea (Åkerlund, *Acta Obstet. Gynecol. Scand.* 66, 459–461 (1987). In particular, vasoconstriction of small uterine arteries by vasopressin and oxytocin is thought to produce tissue ischemia and pain (Jovanovic et al., *Br. J. Pharmacol.* 12, 1468–1474 (91997); Chen et al., *Eur. J. Pharmacol.* 376, 25–51 (1999)).

The administration of oxytocin receptor antagonists to farm animals after fertilization has been found to enhance fertility rates by blocking oxytocin induced luteolysis leading to embryonic loss (Hickey et al., WO 96/09824 A1 (1996), Sparks et al., WO 97/25992 A1 (1997); Sparks et al., U.S. Pat. No. 5,726,172 A (1998)). Thus, oxytocin receptor antagonists can be useful in farm animal husbandry to control timing of parturition and delivery of newborns resulting in enhanced survival rates. They can also be useful for the synchronization of estrus by preventing oxytocin induced corpus luteum regression and by delaying estrus (Okano, *J. Reprod. Dev.* 42 (Suppl.), 67–70 (1996)). Furthermore oxytocin receptor antagonists have been found to have a powerful effect in inhibiting oxytocin-induced milk ejection in dairy cows (Wellnitz et al., *Journal of Dairy Research* 66, 1–8 (1999)).

Oxytocin is also synthesized in the brain and released in the central nervous system. Recent studies have established the importance of central oxytocin in cognitive, affiliative, sexual and reproductive behavior, and in regulating feeding, grooming and response to stress in animals. Oxytocin may also influence normal behavior in humans. Modulators of oxytocin binding to its receptors in the central nervous system may be useful in the prevention and treatment of disfunctions of the oxytocin system, including obsessive compulsive disorder (OCD) and other neuropsychiatric disorders (Kovacs et al., *Psychoneuroendocrinology* 23, 945–962 (1998); McCarthy et al., *U.K. Mol. Med. Today* 3, 269–275 (1997); Bohus, *Peptidergic Neuron, [Int. Symp. Neurosecretion]*, $12^{th}$ (1996), 267–277, Publ. Birkhauser, Basel, Switz.; Leckman et al., *Psychoneuroendocrinology* 19, 723–749 (1994)).

Compounds which act as competitive inhibitors against vasopressin binding to its receptors are useful in the treatment or prevention of state diseases involving vasopressin disorders in mammals, which include vasodilation and aquaresis (free-water diuresis), treating hypertension and inhibiting platelet aggregation. They are useful in the treatment of congestive heart failure, cirrhosis with ascites, and in the syndrome of inappropriate secretion of antidiuretic hormone (SIADH). Furthermore, vasopressin receptor antagonists have been found to be useful in treating disturbances or illnesses of the inner ear, particularly those related to Meniere's disease (Zenner et al., WO 99/24051-A2 (1999)); and for the prevention and treatment of ocular circulatory disorders, particularly intraocular hypertension or glaucoma and vision disorders such as shortsightedness (Ogawa et al., WO 99/38533-A1 (1999)).

SUMMARY OF THE INVENTION

This invention comprises compounds selected from those of Formula (I):

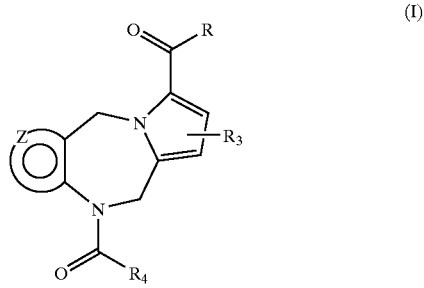

wherein:

$R_1$ and $R_2$ are, independently, selected from hydrogen, ($C_1$-$C_6$)lower alkyl, halogen, cyano, trifluoromethyl, hydroxy, amino, ($C_1$–$C_6$) lower alkylamino, ($C_1$–$C_6$) lower alkoxy, —$OCF_3$, ($C_1$–$C_6$) lower alkoxycarbonyl, —NHCO[($C_1$–$C_6$)lower alkyl], carboxy, —$CONH_2$, —CONH ($C_1$–$C_6$) lower alkyl, or —CON[($C_1$–$C_6$) lower alkyl]$_2$;

$R_3$ is a substituent selected from hydrogen, ($C_1$–$C_6$) lower alkyl, ($C_1$–$C_6$) lower alkoxy, hydroxy, amino, ($C_1$–$C_6$) lower alkylamino, —CO lower alkyl ($C_1$–$C_6$), or halogen;

$R_4$ consists of the moiety B-C;

wherein B is selected from the group of:

(a)

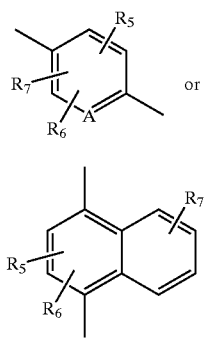

or (b)

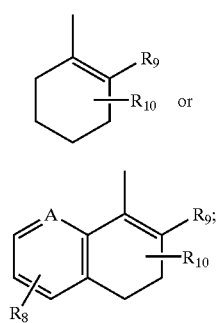

and C is defined as:

(c)

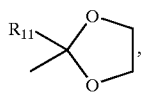

or (d)

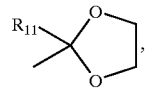

wherein:

A is CH or N;

$R_5$, $R_6$, $R_7$ and $R_8$ are independently, selected from hydrogen, ($C_1$–$C_6$) lower alkyl, ($C_1$–$C_6$) lower alkoxy, hydroxy ($C_1$–$C_6$) lower alkyl, alkoxy ($C_1$–$C_6$) lower alkyl, acyloxy ($C_1$–$C_6$) lower alkyl, ($C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, alkoxycarbonyl, cycloalkyloxycarbonyl, aryl alkyloxycarbonyl, carbamoyl, —O—$CH_2$—CH=$CH_2$, halogen, halo lower alkyl, trifluoromethyl, —$OCF_3$, —S(lower alkyl), —OC(O)N[lower alkyl]$_2$, —CONH (lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, lower alkylaminosulfonyl,

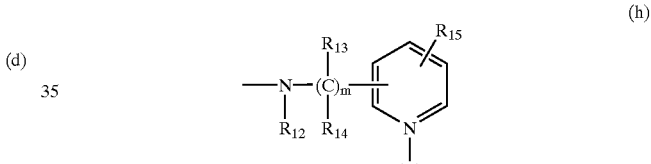

phenyl or naphthyl;

$R_9$ is chosen from the group of hydrogen, lower alkyl, hydroxy ($C_1$–$C_6$) lower alkyl, alkoxy ($C_1$–$C_6$) lower alkyl, acyloxy ($C_1$–$C_6$) lower alkyl, alkoxycarbonyl, —CON[($C_1$–$C_6$) lower alkyl]$_2$, cyano; or aryl, optionally substituted by halogen, or lower alkoxy;

$R_{10}$ represents one to two substituents chosen independently, from the group of hydrogen, lower alkyl, hydroxy ($C_1$–$C_6$) lower alkyl, alkoxy ($C_1$–$C_6$) lower alkyl, acyloxy ($C_1$–$C_6$) lower alkyl, [($C_1$–$C_6$) lower alkyl]$_2$, carbonyl,

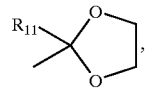

azido, amino, —NH[lower alkyl], —N[lower alkyl]$_2$, amino carbonyl lower alkyl, phthalimido, cyano, halogen, thio lower alkyl, aryloxy, arylthio, aryl optionally substituted with one to three substituents chosen from ($C_1$–$C_6$) lower alkyl, alkoxy or halogen; hydroxy, lower alkoxy, —$OSO_2R_{17}$, or OP' wherein P' is tert-butyl dimethylsilyl, tert-butyl diphenylsilyl, carbonyl loweralkyl, carbonyl trifluoro lower alkyl, aryl lower alkyl, arylcarbonyl, methoxymethyl, or methylthiomethyl; with the proviso that when $R_{10}$ represents two substituents, the two substituents may be joined together to form with the cyclohexene ring to which they are attached a bicyclic system including but not limited to bicyclo[3.2.1]oct-2-ene, or (6,6-dimethyl)-bicyclo [3.1.1]hept-2-ene;

$R_{11}$ is selected from the group of hydrogen, or ($C_1$–$C_6$) lower alkyl; and R is selected from any of the following groups:

(h)

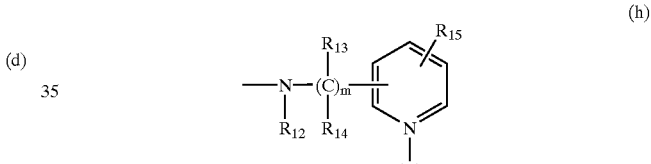

(i)

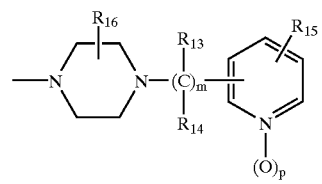

(j)

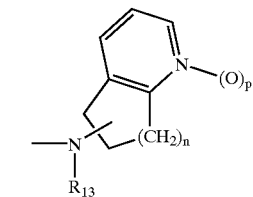

(k)

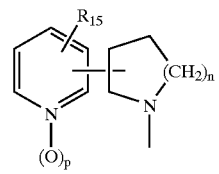

wherein:

$R_{12}$ is selected from the group of hydrogen, ($C_1$–$C_6$) lower alkyl, cyanoethyl or

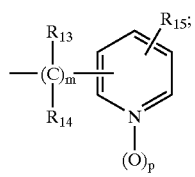

$R_{13}$ and $R_{14}$ are, independently, selected from the group of hydrogen or ($C_1$–$C_6$) lower alkyl;

$R_{15}$ is one or two substituents selected, independently, from the group of hydrogen, ($C_1$–$C_6$) lower alkyl, halogen, trifluoromethyl, ($C_1$–$C_6$) lower alkoxy, ($C_1$–$C_6$) lower alkoxycarbonyl, or

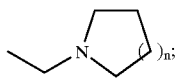

$R_{16}$ represents one to two substituents selected, independently, from hydrogen, or ($C_1$–$C_6$) lower alkyl;

$R_{17}$ is selected from the group of hydrogen, ($C_1$–$C_6$) lower alkyl, trifluoro lower alkyl, or aryl optionally substituted by lower alkyl;

m is an integer from 0 to 2;

n is an integer from 1 to 2;

and p is an integer from 0 to 1;

and the pharmaceutically acceptable salts, or pro-drug forms thereof.

Among the more preferred compounds of this invention are those of the formula:

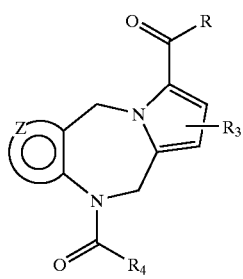

(I)

wherein:

 is

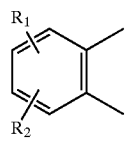 or 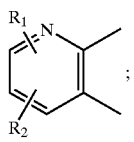 ;

$R_1$ and $R_2$ are, independently, selected from hydrogen, ($C_1$–$C_6$) lower alkyl, halogen, cyano, trifluoromethyl, hydroxy, amino, ($C_1$–$C_6$) lower alkylamino, ($C_1$–$C_6$) lower alkoxy, —$OCF_3$, ($C_1$–$C_6$) lower alkoxycarbonyl, —NHCO[($C_1$–$C_6$)lower alkyl], carboxy, —$CONH_2$, —CONH ($C_1$–$C_6$) lower alkyl, or —CON[($C_1$–$C_6$) lower alkyl]$_2$;

$R_3$ is a substituent selected from hydrogen, ($C_1$–$C_6$) lower alkyl, ($C_1$–$C_6$) lower alkoxy, hydroxy, amino, ($C_1$–$C_6$) lower alkylamino, —CO lower alkyl ($C_1$–$C_6$), or halogen;

$R_4$ consists of the moiety B-C;

wherein B is selected from the group of:

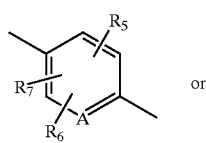

(a)

or

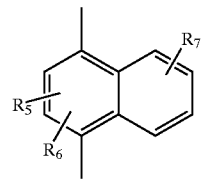

(b)

and C is defined as:

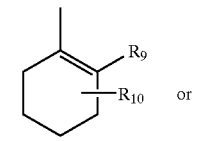

(c)

or

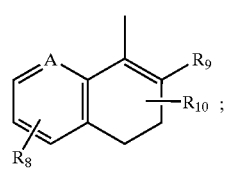

(d)

wherein:

A is CH or N;

$R_5$, $R_6$, $R_7$ and $R_8$ are independently, selected from H, ($C_1$–$C_6$) lower alkyl, ($C_1$–$C_6$) lower alkoxy, hydroxy ($C_1$–$C_6$) lower alkyl, alkoxy ($C_1$–$C_6$) lower alkyl, acyloxy ($C_1$–$C_6$) lower alkyl, ($C_1$–$C_6$) lower alkylcarbonyl, ($C_3$–$C_6$) lower alkenyl, ($C_3$–$C_6$) lower alkynyl, ($C_3$–$C_8$) cycloalkyl, formyl, cycloalkylcarbonyl, carboxy, alkoxycarbonyl, cycloalkyloxycarbonyl, carbamoyl, —O—$CH_2$—CH=$CH_2$, halogen, halo lower alkyl, trifluoromethyl, —$OCF_3$, —S(lower alkyl), —OC(O)N[lower alkyl]$_2$, —CONH(lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, or lower alkylaminosulfonyl;

$R_9$ is chosen from the group of H, lower alkyl, hydroxy ($C_1$–$C_6$) lower alkyl, alkoxy ($C_1$–$C_6$) lower alkyl, acyloxy ($C_1$–$C_6$) lower alkyl, alkoxycarbonyl, —CON[($C_1$–$C_6$) lower alkyl]$_2$, or cyano;

$R_{10}$ represents one to two substituents chosen independently, from the group of hydrogen, lower alkyl, hydroxy ($C_1$–$C_6$) lower alkyl, alkoxy ($C_1$–$C_6$) lower alkyl, acyloxy ($C_1$–$C_6$) lower alkyl, [($C_1$–$C_6$) lower alkyl]$_2$, carbonyl, azido, amino, —NH[lower alkyl], —N[lower alkyl]$_2$, amino carbonyl lower alkyl, phthalimido, cyano, halogen, thio lower alkyl, aryloxy, arylthio, hydroxy, lower alkoxy, —$OSO_2R_{17}$, or OP' wherein P' is tert-butyl dimethylsilyl, tert-butyl diphenylsilyl, carbonyl loweralkyl, carbonyl trifluoro lower alkyl, methoxymethyl, or methylthiomethyl;

$R_{11}$ is selected from the group of hydrogen, or ($C_1$–$C_6$) lower alkyl; and R is selected from any of the following groups:

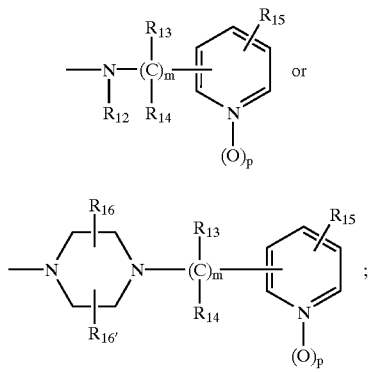

wherein:
$R_{12}$ is selected from the group of hydrogen, or $(C_1-C_6)$ lower alkyl;
$R_{13}$ and $R_{14}$ are independently selected from hydrogen or $(C_1-C_6)$ lower alkyl;
$R_{15}$ is one or two substituents selected, independently, from the group of hydrogen, $(C_1-C_6)$ lower alkyl, halogen, trifluoromethyl, $(C_1-C_6)$ lower alkoxy, $(C_1-C_6)$ lower alkoxycarbonyl;
$R_{16}$ and $R_{16'}$ are selected independently from hydrogen, or $(C_1-C_6)$ lower alkyl;
m is an integer from 0 to 2;
and p is an integer from 0 to 1;
or a pharmaceutically acceptable salt or pro-drug form thereof.

As used herein the term "lower" in relation to alkoxy or alkyl is understood to refer to those groups having from 1 to 6 carbon atoms. Halogen refers to fluorine, chlorine, bromine or iodine.

It is understood by those practicing the art that some of the compounds of this invention depending on the definition of $R_1$, $R_2$, $R_3$, $R_4$ and R may contain one or more asymmetric centers and may thus give rise to enantiomers and diastereomers. The present invention includes all stereoisomers including individual diastereomers and resolved, enantiomerically pure R and S stereoisomers; as well as racemates, and all other mixtures of the R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, E/Z isomers, endo-exo isomers, and mixtures thereof which possess the indicated activity. Such isomers may be obtained in pure form by standard separation procedures known to those skilled in the art. It is understood also by those practicing the art that some of the compounds of this invention depending on the definition of $R_5$, $R_6$, $R_7$, $R_9$ and $R_{10}$ may be chiral due to hindered rotation, and give rise to atropisomers which can be resolved and obtained in pure form by standard procedures known to those skilled in the art. Also included in the present invention are all polymorphs and hydrates of the compounds of the present invention.

DETAILED DESCRIPTION OF THE INVENTION

The present invention comprises the compounds described above, as well as pharmaceutical compositions containing a pharmaceutically or therapeutically effective amount of one or more compounds of this invention in combination or association with one or more pharmaceutically acceptable carriers or excipients. In particular, the present invention provides a pharmaceutical composition which comprises a therapeutically or pharmaceutically effective amount of one or more compounds of this invention and a pharmaceutically acceptable carrier or excipient.

This invention also comprises methods for treating, inhibiting or preventing conditions in a mammal, preferably a human, which are remedied or alleviated by oxytocin antagonist activity including, but not limited to, treatment or prevention of preterm labor, dysmenorrhea and suppressing labor prior to caesarian delivery whenever desirable in a mammal, preferably in a human. The methods comprise administering to a mammal in need thereof a pharmaceutically or therapeutically effective amount of one or more of the compounds of this invention.

The present invention also comprises combinations of the compounds of the present invention with one or more agents useful in the treatment of disorders such as preterm labor, dysmenorrhea, and stopping labor prior to caesarian delivery. More specifically, the compounds of the present invention may be effectively administered in combination with effective amounts of other tocolytic agents used in the treatment or prevention of preterm labor, dysmenorrhea or suppressing labor prior to caesarean delivery including β-adrenergic agonists, calcium channel blockers, prostaglandin synthesis inhibitors, other oxytocin antagonists (e.g. atosiban), magnesium sulfate, ethanol, and other agents useful in the treatment of said disorders. The present invention is to be understood as embracing all simultaneous or alternating treatments of any combination of the compounds of the present invention with other tocolytic agents with any pharmaceutical composition useful for the treatment of preterm labor, dysmenorrhea, and suppressing labor prior to caesarean delivery in mammals.

The compositions are preferably adapted for intravenous (both bolus and infusion) and oral administration. However, they may be adapted for other modes of administration including subcutaneous, intraperitoneal, or intramuscular administration to a human or a farm animal in need of a tocolytic agent.

The compounds of the present invention can be used in the form of salts derived from non toxic pharmaceutically acceptable acids or bases. These salts include, but are not limited to, the following: salts with inorganic acids such as hydrochloric acid, hydrobromic acid, sulfuric acid, nitric acid, phosphoric acid and, as the case may be, such organic acids as acetic acid, oxalic acid, citric acid, tartaric acid, succinic acid, maleic acid, benzoic acid, benzene sulfonic acid, fumaric acid, malic acid, methane sulfonic acid, pamoic acid, and para-toluenesulfonic acid . Other salts include salts with alkali metals or alkaline earth metals, such as sodium, potassium, calcium or magnesium, or with organic bases including quaternary ammonium salts. The compounds can also be used in the form of esters, carbamates and other conventional prodrug forms, which in general, will be functional derivatives of the compounds of this invention which are readily converted to the active moiety in vivo. This is meant to include the treatment of the various conditions described hereinbefore with a compound of this invention or with a compound which is not specifically disclosed but which converts to a compound of this invention in vivo upon administration. Also included are metabolites of the compounds of the present invention defined as active species produced upon introduction of these compounds into a biological system.

When the compounds of this invention are employed for the above utilities, they may be combined with one or more pharmaceutically acceptable excipients or carriers, for example, solvents, diluents and the like, and may be administered orally in such forms as tablets, capsules (including time release and sustained release formulations), pills, dispersible powders, granules, or suspensions containing, for example, from 0.05 to 5% of suspending agent, syrups containing, for example, from about 10 to 50% of sugar, and elixirs and the like, or parenterally in the form of sterile injectable solutions, suspensions or emulsions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredients employed may vary depending on the particular compound or salt employed, the mode of administration, age, weight, sex and medical condition of the patient, and the severity of the condition being treated. An ordinarily skilled physician, veterinarian or clinician can readily determine and prescribe the effective amount of the agent required to prevent, counter or arrest the progress of the condition. However, in general, satisfactory results are obtained when the compounds of the invention are administered at a daily dose of from about 0.5 to about 500 mg/Kg of mammal body weight, preferably given in divided doses two to four times a day, or in a sustained release form. For most large mammals the total daily dosage is from about 0.5 to 100 mg, preferably from 0.5 to 80 mg/Kg. Dosage forms suitable for internal use comprise from about 0.05 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, glycerol, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under conditions of manufacture and storage and must be preserved against the contaminating action of microorganisms such as bacteria and fungi. The carrier can be a solvent or dispersion medium containing, for example, water, ethanol (e.g. glycerol, propylene glycol, and liquid polyethylene glycol), suitable mixtures thereof, and vegetable oil.

Furthermore, active compounds of the present invention can be administered intranasally using vehicles suitable for intranasal delivery, or transdermally using transdermal skin patches known to those ordinarily skilled in the art. When using a transdermal delivery system, the dosage administration will be continuous rather than in a single or divided daily doses. The compounds of the present invention can also be administered in the form of liposome delivery system wherein the liposomal lipid bilayers are formed from a variety of phospholipids.

Compounds of the present invention may also be delivered by the use of carriers such as monoclonal antibodies to which the active compounds are coupled. The compounds of the present invention may also be coupled to soluble polymers as drug carriers or to biodegradable polymers useful in achieving controlled release of the active agent.

Also according to the present invention there are provided processes for producing the compounds of the present invention.

PROCESS OF THE INVENTION

The compounds of the present invention may be prepared according to one of the general processes outlined below.

The compounds of general formula (I) wherein

R, $R_3$, and $R_4$ are defined hereinbefore, can be conveniently prepared as shown in Scheme I.

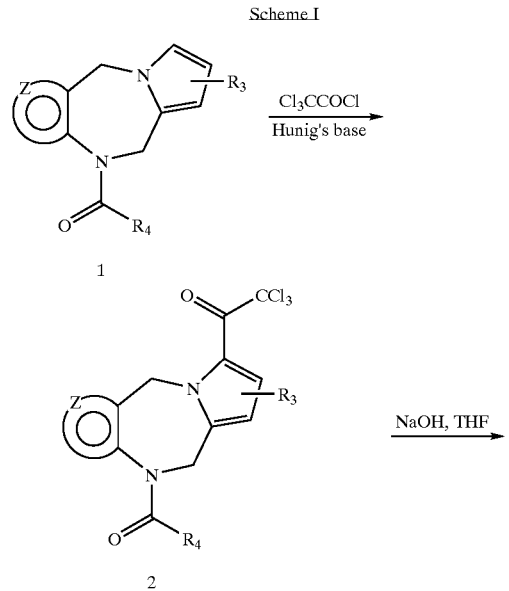

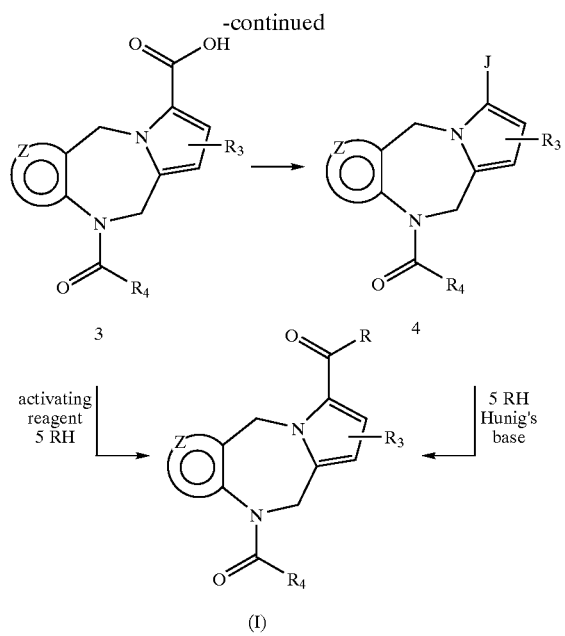

According to the above preferred process, a tricyclic diazepine of formula (1) wherein

$R_3$ and $R_4$ are defined hereinbefore, is reacted with perhaloalkanoyl halide preferably trichloroacetyl chloride in the presence of an organic base such as N,N-diisopropylethyl amine (Hünig's base) in an aprotic organic solvent such as dichloromethane at temperatures ranging from −10° C. to ambient to provide the desired trichloroacetyl intermediate of formula (2). Subsequent hydrolysis of (2) with aqueous base such as sodium hydroxide in an organic solvent such as tetrahydrofuran or acetone at temperatures ranging from −10° C. to ambient, yields the intermediate acid of formula (3). The required activation of the carboxylic acid (3) for the subsequent coupling with a primary or secondary amine of formula (5) can be accomplished in several ways. Thus, (3) can be converted to an acid halide preferably a chloride or bromide of formula (4, J=COCl or COBr) by reaction with thionyl chloride(bromide) or oxalyl chloride(bromide) or similar reagents known in the art, either neat or in the presence of an inorganic base such as potassium carbonate, or in the presence of an organic base such as pyridine, 4-(dimethylamino)pyridine, or a tertiary amine such as triethylamine in an aprotic solvent such as dichloromethane, N,N-dimethylformamide or tetrahydrofuran at temperatures ranging from −5° C. to 50° C. to yield the intermediate acylated derivative (4). Subsequent coupling of the acid chloride(bromide) (4, J=COCl or COBr) with an appropriately substituted primary or secondary amine of formula (5) in the presence of a stoichiometric amount of Hünig's base in an aprotic solvent such as dichloromethane, N,N-dimethylformamide or tetrahydrofuran at temperatures ranging from ambient to the reflux temperature of the solvent provides the desired compounds of formula (I) wherein

R, $R_3$ and $R_4$ are as defined hereinbefore.

Alternatively, the acylating species can be a mixed anhydride of the corresponding carboxylic acid, such as that prepared by treating said acid of formula (3) with 2,4,6-trichlorobenzoyl chloride in an aprotic organic solvent such as dichloromethane according to the procedure of Inanaga et al., *Bull. Chem. Soc. Jpn.* 52, 1989 (1979). Treatment of said mixed anhydride of formula (4) with an appropriately substituted primary or secondary amine of formula (5) in an aprotic solvent such as dichloromethane at temperatures ranging from ambient to the reflux temperature of the solvent provides the desired compounds of formula (I) wherein

R, $R_3$ and R4 are as defined hereinbefore.

Alternatively, amidation of the carboxylic acids of formula (3) can be effectively carried out by treatment of said acid with triphosgene in an aprotic solvent such as dichloromethane followed by reaction of the activated intermediate with an appropriately substituted primary or secondary amine of formula (5) in the presence of an organic base such as Hünig's base at temperatures ranging from −10° C. to ambient.

Another preferred process for the preparation of the compounds of the present invention of formula (I) wherein

R, $R_3$ and $R_4$ are as defined hereinbefore, consists of treating the acid of formula (3) with an activating reagent such as N,N-dicyclohexylcarbodiimide or 1-ethyl-3-(3-dimethylamino-propyl) carbodiimide hydrochloride in the presence of 1-hydroxybenzotriazole followed by reaction of the activated intermediate with an appropriately substituted primary or secondary amine of formula (5) preferably in the presence of an organic base such as Hünig's base and a catalytic amount of 4-(dimethylamino)pyridine in an aprotic solvent such as dichloromethane, N,N-dimethylformamide or tetrahydrofuran at temperatures ranging from −10° C. to ambient.

In another preferred process, said acid (3) can be activated by treatment with other activating agents such as N,N'-carbonyidiimidazole in an aprotic solvent such as dichloromethane or tetrahydrofuran at temperatures ranging from −10° C. to the reflux temperature of the solvent. Subsequent reaction of the intermediate activated imidazolide with an appropriately substituted primary or secondary amine of formula (5) provides the desired compounds of formula (I) wherein

R, $R_3$ and $R_4$ are as defined hereinbefore.

Alternatively, the coupling of the appropriately substituted primary or secondary amine of formula (5) with said acid of formula (3) can be effectively carried out by using hydroxybenzotriazole tetramethyluronium hexafluorophosphate as the coupling reagent in the presence of an organic base such as Hünig's base and in a solvent such as N,N-dimethylformamide at temperatures ranging from −10° C. to ambient to provide in good isolated yield and purity the desired compounds of formula (I) wherein

R, $R_3$ and $R_4$ are as defined hereinbefore.

Related coupling reagents such as diphenylphosphoryl azide, diethyl cyano phosphonate, benzotriazol-1-yl-oxy-tris-(dimethylamino) phosphonium hexafluorophosphate and all other known reagents in the literature that have been used in the formation of amide bonds in peptide synthesis can also be used for the preparation of compounds of formula (I) wherein

R, $R_3$ and $R_4$ are as defined hereinbefore.

As an alternative, reaction of the intermediate 3-trihalomethylketone of formula (2) directly with an appropriately substituted primary or secondary amine of formula (5) also provides the desired compounds of formula (I) wherein

R, $R_3$ and $R_4$ are as defined hereinbefore.

The method of choice for the preparation of compounds of formula (I) from the intermediate carboxylic acid (3) is ultimately chosen on the basis of its compatibility with the R, $R_3$ and $R_4$ groups, and its reactivity with the tricyclic benzodiazepine of formula (1).

Another preferred process for the preparation of (I) of Scheme I is shown in Scheme II. A tricyclic diazepine of formula (1) is reacted with diphosgene in an aprotic solvent such as dichloromethane preferably in the presence of an organic base such as triethylamine, followed by reaction of the resulting acylated intermediate with an appropriately substituted primary or secondary amine of formula (5) to provide the desired compounds of formula (I) wherein

R, $R_3$ and $R_4$ are as defined hereinbefore.

Scheme II

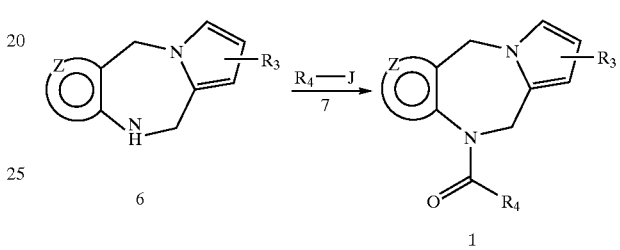

1. Diphosgene, TEA
2. TEA, RH (5)

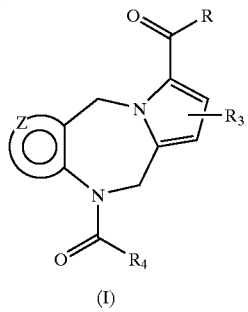

(I)

The tricyclic diazepines of formula (1) of Scheme (I) wherein $R_4$ is defined hereinbefore, can be conveniently prepared as shown in Scheme III.

Scheme III

Thus, a tricyclic diazepine of formula (6) is treated with an appropriately substituted acylating agent such as an aroyl halide, preferably an appropriately substituted acyl chloride or bromide of formula (7, J=COCl or COBr) wherein $R_4$ is ultimately chosen on the basis of its compatibility with the present reaction scheme, in the presence of an inorganic base such as potassium carbonate, or in the presence of an organic base such as pyridine, 4-(dimethylamino)pyridine, or a tertiary amine such as triethylamine or N,N-diisopropylethyl amine in an aprotic solvent such as dichloromethane, N,N-dimethylformamide or tetrahydrofuran, at temperatures ranging from −5° C. to 50° C. to provide intermediates of general formula (1) wherein $R_4$ is defined hereinbefore.

Alternatively, the acylating species of formula (7) can be a mixed anhydride of the corresponding carboxylic acid, such as that prepared by treating said acid with 2,4,6-trichlorobenzoyl chloride in an aprotic organic solvent such as dichloromethane according to the procedure of Inanaga et al., *Bull. Chem. Soc. Jpn.*, 52, 1989 (1979). Treatment of said mixed anhydride of general formula (7) with a tricyclic diazepine of formula (6) in a solvent such as dichloromethane and in the presence of an organic base such as 4-(dimethylamino)pyridine at temperatures ranging from 0° C. to the reflux temperature of the solvent, yields the intermediate acylated derivative (1) of Scheme III.

The acylating intermediate of formula (7) is ultimately chosen on the basis of its compatibility with the $R_4$ groups, and its reactivity with the tricyclic diazepine of formula (6).

The desired intermediates of formula (7) of Scheme III wherein $R_4$ consists of the moiety B-C wherein B is (a) and C is (c) can be conveniently prepared by a process shown in Scheme IV. Thus, an appropriately substituted aryl (heteroaryl) iodide(bromide, chloride, or trifluoromethanesulfonate) of formula (8) wherein P is a carboxylic acid protecting group, preferably P=alkyl or benzyl, M=I, Br, Cl, or OTf, and A, $R_5$, $R_6$ and $R_7$ are defined hereinbefore, is reacted with a tri(alkyl)tin(IV) derivative of formula (9, W=Sn(trialkyl)$_3$, preferably Sn(n-Bu)$_3$) wherein $R_9$, $R_{10}$ are ultimately chosen on the basis of their compatibility with the present reaction scheme, in the presence of a Pd(0) catalyst, and in the presence or absence of inorganic salts (e.g. LiCl), in an aprotic solvent such as dioxane or N-methylpyrrolidinone, to provide the intermediate ester (10). Subsequent unmasking of the carboxylic function by hydrolysis, hydrogenolysis or similar methods known in the art, followed by activation of the intermediate acid (11) provide the desired compounds of formula (19) wherein A, $R_5$, $R_6$, $R_7$, $R_8$, $R_9$ and $R_{10}$ are hereinbefore defined, suitable for coupling with the tricyclic diazepine of formula (6).

or water-acetonitrile at temperatures ranging from ambient to the reflux temperature of the solvent (Suzuki, *Pure & Appl. Chem.* 66, 213–222 (1994), Badone et al., *J. Org. Chem.* 62, 7170–7173 (1997); Wolfe et al. *J. Am. Chem. Soc.* 121, 9559 (1999); Shen, *Tetr. Letters* 38, 5575 (1997)). The exact conditions for the Suzuki coupling of the halide and the boronic acid intermediates are chosen on the basis of the nature of the substrate and the substituents. The desired intermediates of formula (10) of Scheme IV can be similarly prepared from the bromide (8, M=Br) and the boronic acid

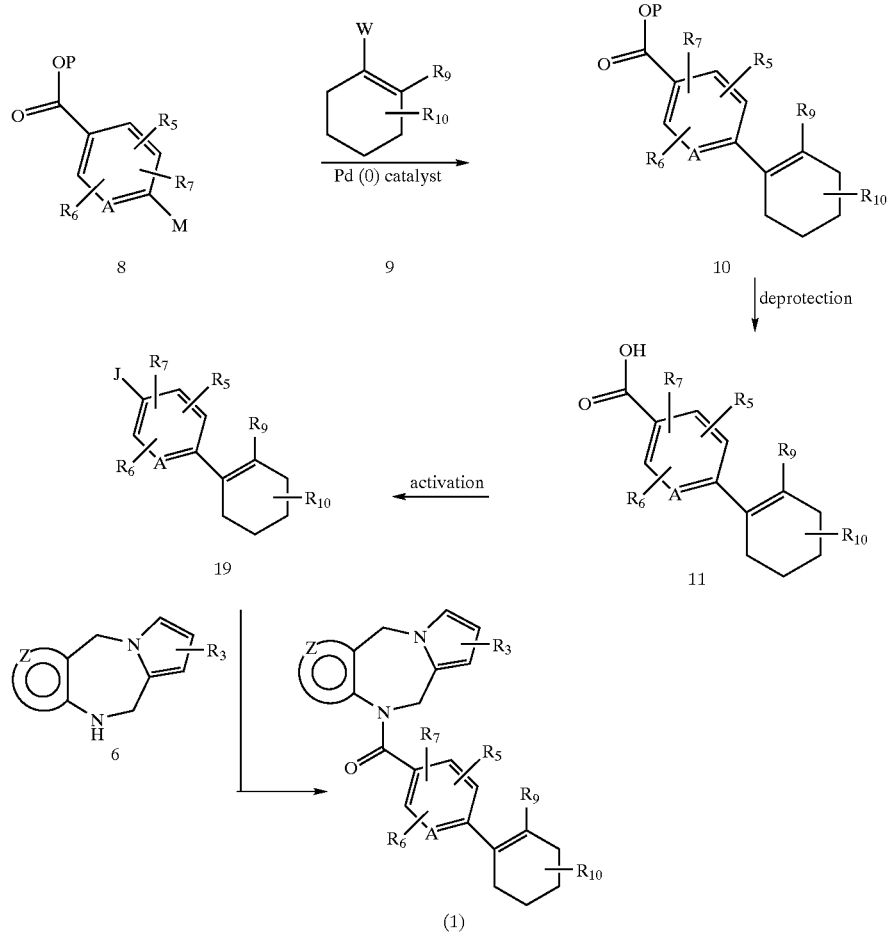

The desired intermediates of formula (7) of Scheme III wherein $R_4$ consists of the moiety B-C where B is (a) and C is (d) or B is (b) and C is either (c) or (d) can be prepared by a process analogous to that exemplified in Scheme IV by replacing intermediates of formulas (8 and 9) with appropriately substituted naphthyl, dihydronaphthyl or dihydroquinolinyl intermediates.

Alternatively, the desired intermediates of formula (10) of Scheme IV wherein $R_4$ consists of the moiety B-C where B is (a) and C is (c) can be prepared by Suzuki coupling from the iodide(bromide, chloride, or trifluoromethanesulfonate) (8, M=I, Br, Cl, or OTf) and an appropriately substituted boron derivative of formula (9, preferably W=B(OH)$_2$) in the presence of a palladium catalyst such as palladium(II) acetate or tetrakis(triphenylphosphine) palladium(0) and an organic base such as triethylamine or an inorganic base such as sodium(potassium or cesium) carbonate with or without added tetrabutylammonium bromide(iodide), in a mixture of solvents such as toluene-ethanol-water, acetone-water, water (9) in a solvent such as dioxane, N,N-dimethylformamide or dimethylsulfoxide in the presence of potassium phosphate and a Pd(0) catalyst.

Alternatively, a cross coupling reaction of an iodide (bromide or trifluoromethanesulfonate) of formula (9, W=Br, I, OTf) with a bis(pinacolato)diboron [boronic acid, or trialkyl tin(IV)] derivative of formula (8,

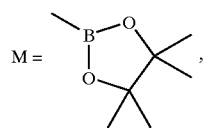

B(OH)$_2$, or SnBu$_3$) yields the desired intermediate of formula (10) which is converted to (I) in the manner of Scheme IV.

The desired intermediates of formula (10) of Scheme IV wherein $R_4$ consists of the moiety B-C wherein B is (a) and C is (d) or B is (b) and C is either (c) or (d) can be prepared in analogous fashion by replacing intermediates of formulas (8 and 9) with appropriately substituted naphthyl, dihydronaphthyl, or dihydroquinolyl intermediates.

The required appropriately substituted aryl(heteroaryl) halides of formula (8, M=Br or I) of Scheme IV are either available commercially, or are known in the art or can be readily accessed in quantitative yields and high purity by diazotization of the corresponding substituted anilines (8, P=H, alkyl or benzyl, M=NH$_2$) followed by reaction of the intermediate diazonium salt with iodine and potassium iodide in aqueous acidic medium essentially according to the procedures of Street et al,. *J. Med. Chem.* 36, 1529 (1993) and Coffen et al., *J. Org. Chem.* 49, 296 (1984) or with copper(I) bromide, respectively (March, *Advanced Organic Chemistry*, 3$^{rd}$ Edn., p.647–648, John Wiley & Sons, New York (1985).

Alternatively, the desired intermediates of formula (11, A=CH) of Scheme IV wherein R$_4$ consists of the moiety B-C wherein B is (a), A=CH) and C is (c) can be conveniently prepared as shown in Scheme V by cross-coupling reaction of an appropriately substituted pinacolato borane of formula (13) wherein R$_9$, R$_{10}$ are ultimately chosen on the basis of their compatibility with the present reaction scheme, with an aryl triflate of formula (14, Y=OTf) or an aryl halide (14, Y=Br, I) wherein R$_5$, R$_6$ and R$_7$ are defined hereinbefore, according to the general procedures of Ishiyama et al., *Tetr. Lett.* 38, 3447–3450 (1997) and Giroux et al. *Tetr. Lett.* 38, 3841–3844 (1997), followed by basic or acidic hydrolysis of the intermediate nitrile of formula (15) (cf. March, *Advanced Organic Chemistry*, 3$^{rd}$ Edn., John Wiley & Sons, New York, p. 788 (1985)).

Scheme V

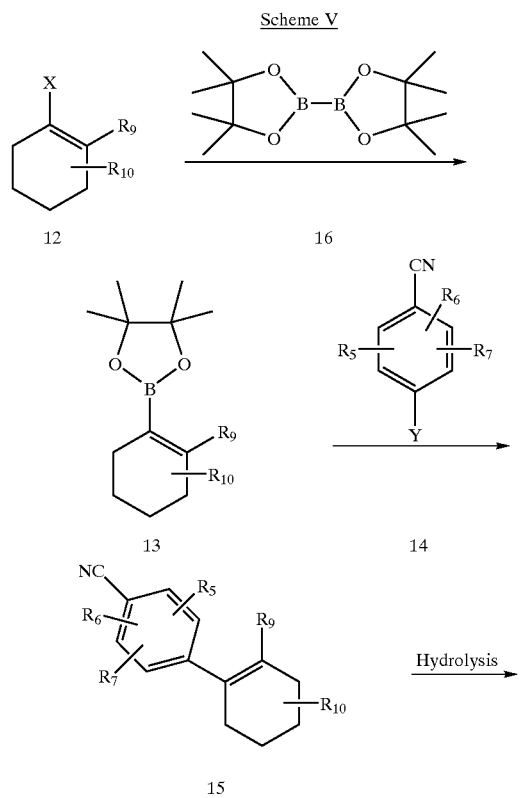

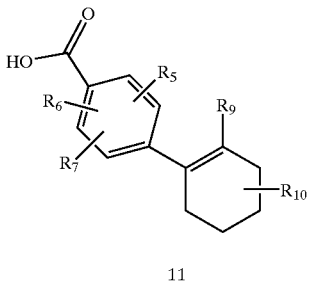

Alternatively, reaction of an iodide (bromide, or trifluoromethanesulfonate) of formula (12, X=Br, I, or OTf) with a bis(pinacolato)diboron [boronic acid or trialkyl tin (IV)] derivative of formula (14,

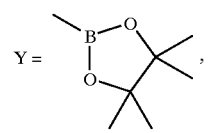

B(OH)$_2$, or SnBu$_3$) yields the desired intermediate of formula (15) which is converted to (11) in the manner of Scheme V.

The desired intermediates of formula (11) of Scheme IV wherein R$_4$ consists of the moiety B-C wherein B is (a, A=CH) and C is (d) or B is (b) and C is either (c) or (d, A=CH), can be prepared in analogous fashion by replacing intermediates of formulas (13 and 14) with appropriately substituted naphthyl or dihydronaphthyl intermediates.

The desired boronic esters of formula (13) of Scheme V can be conveniently prepared by the palladium-catalyzed cross-coupling reaction of the pinacol ester of diboronic acid (16) with an appropriately substituted alkenyl halide preferably a bromide or iodide (12, X=Br, I) or alkenyl trifluoromethanesulfonate (12, X=OTf) according to the described procedures of Ishiyama et al., *J. Org. Chem.* 60, 7508–7510 (1995) and Giroux et al., *Tetr. Lett.* 38, 3841–3844 (1997).

The desired compounds of formula (1) of Scheme IV wherein R$_4$ consists of the moiety B-C wherein B is (a) and C is (c) can be alternatively prepared by a process shown in Scheme VI.

Scheme VI

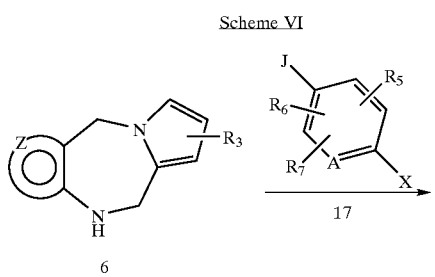

-continued

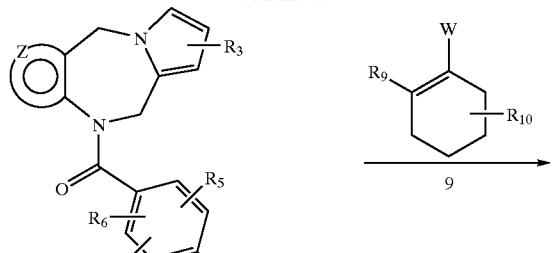

18

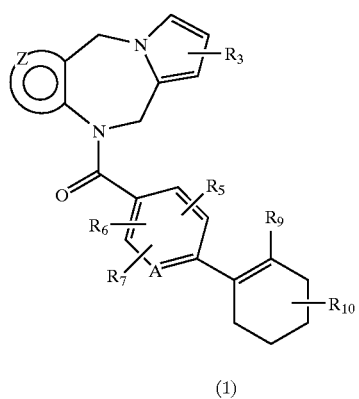

(1)

Thus, a tricyclic diazepine of formula (6) is treated with an appropriately substituted acylating agent such as a halo aroyl(heteroaroyl)halide, preferably an iodo(bromo) aroyl (heteroaroyl) chloride(bromide) of formula (17, J=COCl or COBr; X=I, Br) wherein A, $R_5$, $R_6$ and $R_7$ are hereinbefore defined using any of the procedures hereinbefore described, to provide the acylated intermediate of general formula (18) of Scheme VI.

Alternatively, the acylating species of formula (17) can be a mixed anhydride of the corresponding carboxylic acid. Treatment of said mixed anhydride of general formula (17) with a tricyclic diazepine of formula (6) according to the procedure described hereinbefore yields the intermediate acylated derivative (18).

The acylating intermediate of formula (17) is ultimately chosen on the basis of its compatibility with A and the $R_5$, $R_6$ and $R_7$ groups, and its reactivity with the tricyclic diazepine of formula (6).

A Stille coupling reaction of (18, X=I) with an appropriately substituted organotin reagent such as a trialkyltin (IV) derivative, preferably a tri-n-butyltin(IV) derivative of formula (9, W=SnBu₃) wherein $R_9$, and $R_{10}$ are ultimately chosen on the basis of their compatibility with the present reaction scheme, in the presence of a catalyst such as tetrakis (triphenylphosphine) palladium (0), in an aprotic organic solvent such as toluene or N,N-dimethylformamide, at temperatures ranging from ambient to 150° C. (cf. Farina et al., J. Org. Chem, 59, 5905 (1994) and references cited therein) affords the desired compounds of formula (1) wherein A, $R_3$, $R_5$, $R_6$, $R_7$, $R_7$, $R_9$ and $R_{10}$ are as defined hereinbefore.

Alternatively, reaction of a compound of formula (18, X=Cl, Br or I) with an appropriately substituted cyclohexene boronic acid of formula (9, W=B(OH)₂) wherein $R_9$ and $R_{10}$ chosen on the basis of their compatibility with the reaction scheme, in a mixture of solvents such as toluene-ethanol-water, and in the presence of a Pd(0) catalyst and a base such as sodium carbonate, at temperatures ranging from ambient to the reflux temperature of the solvent, yields the desired compounds of formula (1) wherein

A, $R_3$, $R_5$, $R_6$, $R_7$, $R_9$ and $R_{10}$ are as defined hereinbefore.

Alternatively, a cross-coupling reaction of a compound of formula (18, X=Br or I) with a bis(pinacolato) diboron of formula (16) in the presence of a catalyst such as dichloro-[1,1'-bis(diphenylphosphino)ferrocene]palladium(II) dichloromethane adduct and potassium acetate in an aprotic solvent such as dimethylsulfoxide at temperatures ranging from ambient to 100° C., yields the intermediate of formula

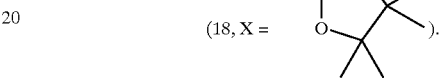

Subsequent reaction of (18) with an appropriately substituted trifluoromethanesulfonate of formula (9, W=OTf) in the presence of a base such as aqueous sodium carbonate in an aprotic solvent such as N,N-dimethylformamide at temperatures ranging from ambient to the reflux temperature of the solvent, provides the desired compounds of formula (1) wherein

A, $R_3$, $R_5$, $R_6$, $R_7$, $R_9$, and $R_{10}$ are as defined hereinbefore.

The preferred substituted aroyl(heteroaroyl) chlorides (bromides) of formula (17) of Scheme VI (X=I, Br; J=COCl or COBr) wherein A, $R_5$, $R_6$ and $R_7$ are as defined hereinbefore, are either available commercially, or are known in the art, or can be readily prepared by procedures analogous to those in the literature for the known compounds.

The intermediates of formula (9, W=Sn(alkyl)₃, alkyl= n-butyl) of Scheme VI are either commercially available or can be conveniently prepared as shown in Scheme VII from the corresponding bromo starting materials of formula (20) wherein $R_9$, $R_{10}$ are ultimately chosen on the basis of their compatibility with the reaction scheme, by first reacting them with n-butyl lithium followed by reaction of the intermediate lithiated species with a trialkyl (preferably trimethyl or tri-n-butyl)tin(IV) chloride).

Scheme VII

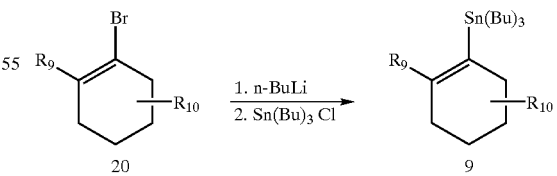

The preferred substituted boronic acids of formula (9, W=B(OH)₂) are either available commercially, or are known in the art, or can be readily prepared by procedures analogous to those in the literature for the known compounds.

The desired compounds of formula (1) of Scheme VI wherein $R_4$ consists of the moiety B-C wherein B is (a) and C is (d) or B is (b) and C is either (c) or (d) can be prepared in analogous fashion by replacing intermediates of formulas (17 and 9) with appropriately substituted naphthyl, dihydronaphthyl or dihydroquinolinyl intermediates.

Alternatively, as shown in Scheme VIII, the appropriately substituted aroyl(heteroaroyl) halides, preferably aroyl (heteroaroyl) chlorides of formula (21, J=COCl) where A, $R_5$, $R_6$ and $R_7$ are hereinbefore defined, are reacted with a tricyclic diazepine of formula (6) to provide the intermediate bromides of formula (22). Subsequent reaction of (22) with a bis-alkyl-tin reagent (preferably bis-(tri-n-butyl)-tin(IV)) in the presence of a Pd(0) catalyst such as tetrakis (triphenylphosphine) palladium(0) and lithium chloride, provides the stannane intermediate of formula (23). Further reaction of the tri-n-butyl tin(IV) derivative (23) with the appropriately substituted alkenyl halide of formula (24, M=Br or I) wherein $R_9$, $R_{10}$ are ultimately chosen on the basis of their compatibility with the present reaction scheme, in the presence of a Pd(0) catalyst such as tetrakis (triphenylphosphine) palladium(0), yields the desired compounds of formula (1) wherein $R_4$ consists of the moiety B-C wherein B is (a) and C is (c), and

A and $R_5$, $R_6$, $R_7$, $R_9$ and $R_{10}$ are defined hereinbefore.

Scheme VIII

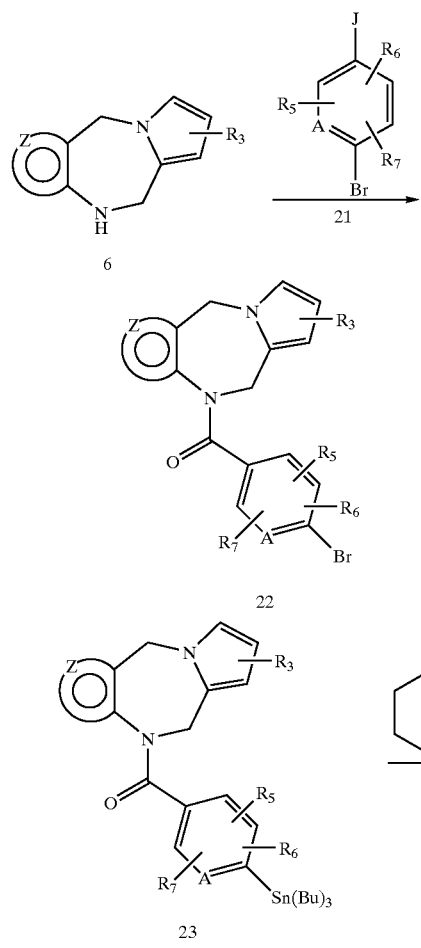

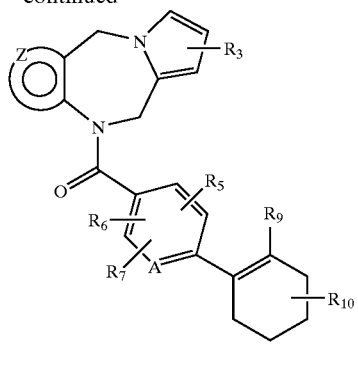

(1)

The desired compounds of formula (1) of Scheme VIII wherein $R_4$ consists of the moiety B-C wherein B is (a) C is (d) and B is (b) and C is either (c) or (d) can be prepared in analogous fashion by replacing intermediates of formulas (21 and 24) with appropriately substituted naphthyl, dihydronaphthyl or dihydroquinolinyl intermediates.

A preferred process for the preparation of the compounds of formula (1) of Scheme I wherein

$R_3$, $R_5$, $R_6$ and $R_7$ are defined hereinbefore, and $R_4$ consists of the moiety B-C wherein B is (a, A=CH) and C is (c), and $R_{10}$ is hydroxy, alkoxy, OP', azido, phthalimido, cyano, phenoxy, thiophenoxy, thioalkyl, and related nucleophiles, is shown in Scheme IX.

Scheme IX

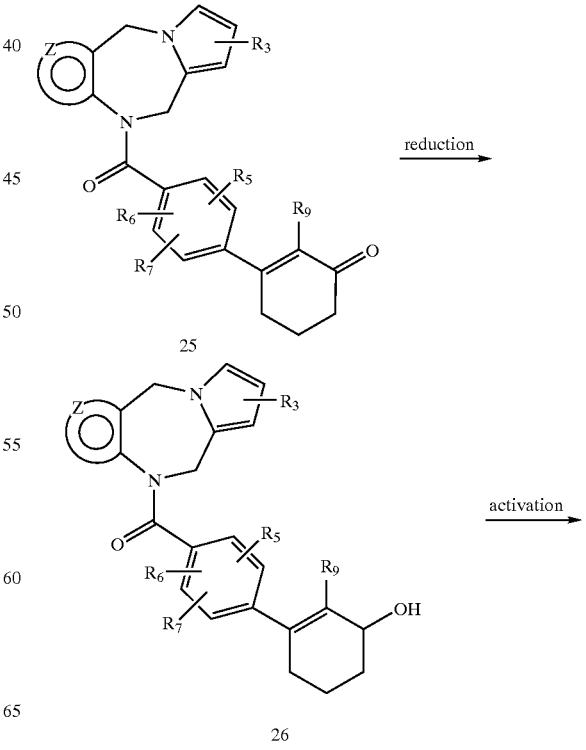

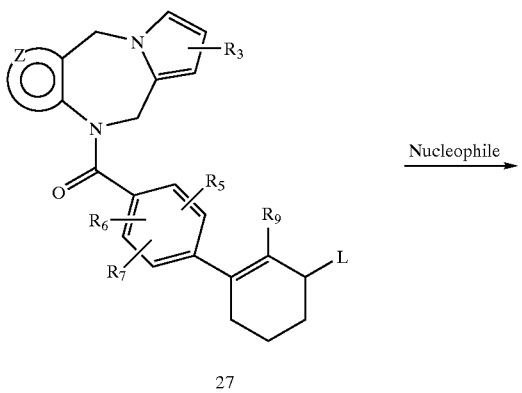

27

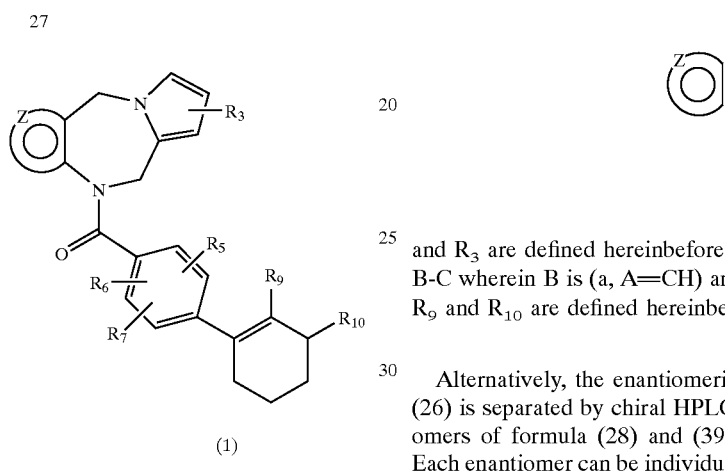

(1)

According to the preferred process, an appropriately substituted diazepine cyclohexenone of formula (25) is converted to the corresponding cyclohexenol (26) by reduction with a metal hydride preferably sodium borohydride in the presence of cerium (III) chloride, in an hydroxylic solvent such as methanol, at temperatures ranging from −78° C. to ambient. The hydroxy function of (26) is then activated by conversion to a leaving group (27, L=leaving group) preferably a para-toluenesulfonate, methanesulfonate, trifluoromethanesulfonate, phosphate and the like. $S_N2$ displacement of the leaving group with a nucleophile such as azide, phthalimide, cyanide, halide, phenol, carbon or sulfur nucleophiles and the like, provides the desired compound (1) wherein and $R_3$ are defined hereinbefore, $R_4$ consists of the moiety B-C wherein B is (a, A=CH) and C is (c), and $R_5$, $R_6$, $R_7$, $R_9$ and $R_{10}$ are defined hereinbefore.

Alternatively, the enantiomeric cyclohexenol of formula (26) is separated by chiral HPLC into its respective enantiomers of formula (28) and (39) according to Scheme X. Each enantiomer can be individually activated and subjected to $S_N2$ displacement with a nucleophile in the manner of Scheme IX.

Scheme X

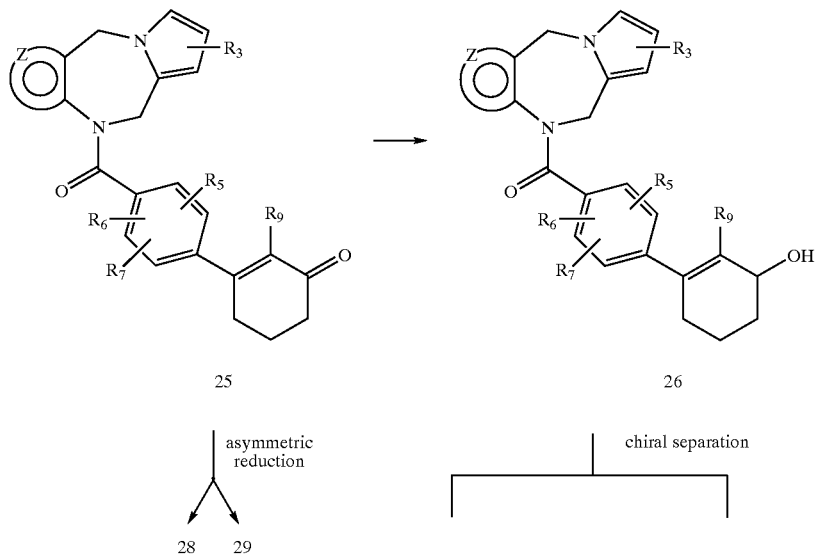

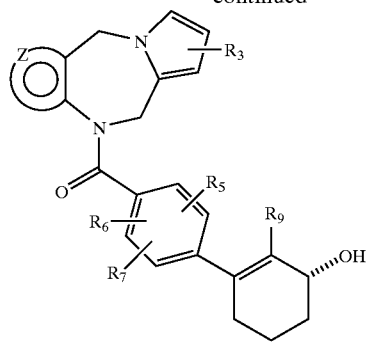

28

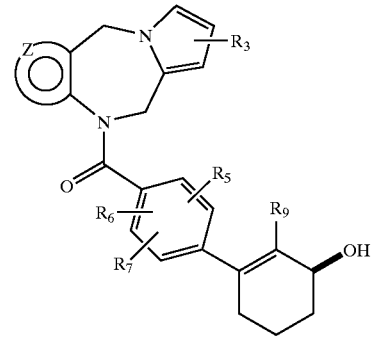

29

-continued

Alternatively, the enantiomeric cyclohexenols of formula (28) and (29) are obtained by asymmetric reduction of the cyclohexenone of formula (25) with a borane-tetrahydrofuran complex in an aprotic solvent such as tetrahydrofuran in the presence of a chiral auxiliary such as (S)-tetrahydro-1-methyl-3,3-diphenyl-1H,3H-pyrrolo[1,2-c][1,3,2]oxazaborole or (R)-tetrahydro-1-methyl-3,3-diphenyl-1H,3H-pyrrolo[1,2-c][1,3,2]oxazaborole respectively, at ambient temperature.

Preferred processes for the preparation of compounds of formula (I) of Scheme I wherein $R_4$ consists of the moiety B-C wherein B is (a) and C is (d) or B is either (b) or (c) and

A, R, $R_3$, $R_5$, $R_6$, $R_7$ are defined hereinbefore, and wherein $R_9$ and $R_{10}$ are ultimately chosen on the basis of their compatibility with the reaction scheme, also utilize acylation of the amide intermediate (30) with an acylating agent of formula (17) of Scheme VI, as shown in Scheme XI.

Scheme XI

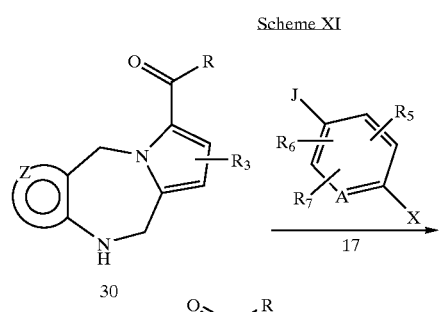

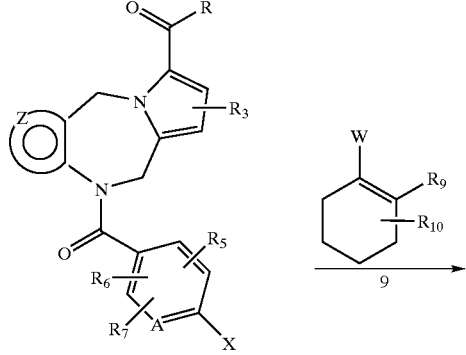

31

-continued (I)

Alternatively, the preferred compounds of formula (I) of scheme I wherein $R_4$ consists of the moiety B-C wherein B is (a) and C is (c) and

A, R, $R_3$, $R_5$, $R_6$, $R_7$ are defined hereinbefore, and wherein $R_9$, $R_{10}$ are ultimately chosen on the basis of their compatibility with the reaction scheme, can be prepared in the manner of Scheme VIII by acylation of the amide intermediate (30) of Scheme XI with an acylating agent of formula (21), as shown in Scheme XII.

Scheme XII

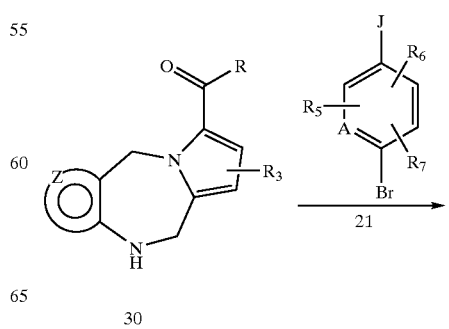

30

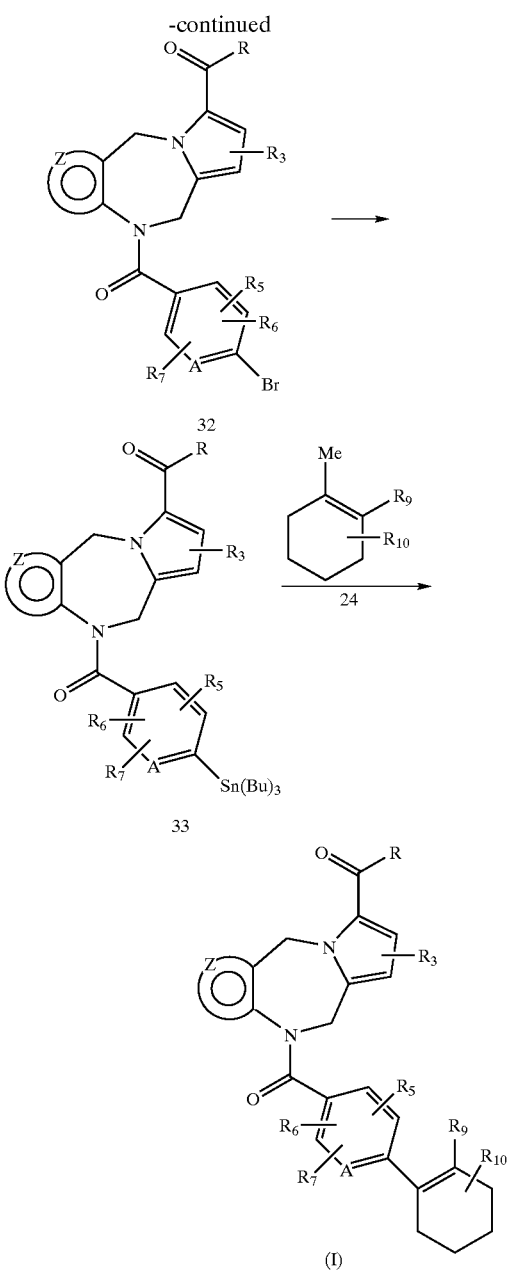

The subject compounds of the present invention were tested for biological activity according to the following procedures.

Vasopressin Binding in Chinese Hamster Ovary Cell Membranes Expressing Human Vasopressin $V_{1a}$ Subtype Receptors Receptor Source:

Chinese hamster ovary cells (CHO cells) stably transfected with the human vasopressin $V_{1a}$ subtype receptors were either obtained from Biosignal Inc., 1744 rue Williams, Montreal, Quebec, Canada or obtained from M. Thibonnier, Case Western Reserve University School of Medicine, Cleveland, Ohio.

A. Passaging and Amplification of Cells:

CHO cells transfected with the human vasopressin $V_{1a}$ subtype receptors obtained from M. Thibonnier (pZeoSV vector) are allowed to grow to confluency (approx. >90%) in T-150 flasks under sterile conditions, in a cell culture medium consisting of F-12 Nutrient Mixture (HAM) with L-glutamine (Gibco Cat. # 11765–054) containing 15 mM HEPES (Gibco Cat. # 15630-080), 1% antibiotic/antimycotic (add 5 mL 100×, Gibco Cat. # 15240-062 per 500 mL F-12), 250 μg/mL Zeocin (add 1.25 mL of 100 mg/mL Invitrogen R-250-01 per 500 mL F-12) and 10% Fetal Bovine Serum (Qualified, heat inactivated, Gibco Cat. # 16140-063). The medium is removed by aspiration and the cells are washed with 10 mL of Hank's Balanced Salt solution (Gibco Cat. # 14175-095). The salt solution is removed by aspiration and the cells are trypsinized with 5 mL of trypsin-EDTA (0.05% trypsin, 0.53 mM EDTA-4Na, Gibco Cat. # 25300-070) for 1 min. The trypsin is removed by aspiration and the cells dislodged by tapping. Cell Culture medium (eg, 30 mL for 1:30 split) is immediately added and mixed well to inactivate trypsin. 1 mL of detached cells is added to new culture flasks containing fresh cell culture medium (eg, into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g,. use 10 mL per T-150 flask). The excess is removed and the cells are bathed for 15–30 min. in an enzyme-free Cell Dissociation Buffer (e.g. use 8 mL Hank's Based, Gibco Cat. # 13150-016 per T-150 flask) until the cells are loosened. The contents are transferred to centrifuge tubes (50 mL) kept an ice bath. All subsequent steps are done at 4° C. The tubes are centrifuged at 300×g for 15 min (1380 rpm on SORVAL, Model RT6000D, using the rotor for 50 mL tubes). The supernatant is discarded and the cells suspended in homogeneizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using the rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 8Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 0.1% of 5 mM $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 μL of unlabeled Manning ligand (to give a final concentration of 0.1 to 10 nM for standard curve and 1000 nM for non specific binding) or test compounds in 50% DMSO (e.g.

for final concentrations of 0.1 to 1000 nM or as appropriate) or 50% DMSO as vehicle control. 20 μL of 50% DMSO is added for Manning and other peptide ligands and the assay buffer volume is adjusted accordingly. To each well is added 50 μL of frozen membrane suspension thawed immediately prior to use and diluted in the assay buffer to the required concentration (equivalent to 25 to 50 μg of protein/well as needed). 20 μL of 8 nM [$^3$H]Manning ligand in the assay buffer, prepared just before use, is added, and incubated at room temperature for 60 min. shaking the plate on a mechanical shaker for the first 15 min. The incubation is stopped by rapid filtration of the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Vasopressin Binding in Chinese Hamster Ovary Cell Membranes Expressing Human Vasopressin $V_2$ Subtype Receptors Receptor Source:

Chinese Hamster Ovary (CHO) cells stably transfected with the human $V_2$ subtype receptors were obtained from M. Thibonnier, Case Western Reserve University School of Medicine, Cleveland, Ohio.

A. Passaging and Amplification of Cells:

CHO cells transfected with the human vasopressin $V_2$ subtype receptors obtained from M. Thibonnier (pZeoSV vector) are allowed to grow to confluency (approx. >90%) in T-150 flasks under sterile conditions, in a cell culture medium consisting of F-12 Nutrient Mixture (HAM) with L-glutamine (Gibco Cat. # 11765-054) containing 15 mM HEPES (Gibco Cat. # 15630-080), 1% antibiotic/antimycotic (add 5 mL 100×, Gibco Cat. # 15240-062 per 500 mL F-12), 250 μg/mL Zeocin (add 1.25 mL of 100 mg/mL Invitrogen R-250-01 per 500 mL F-12) and 10% Fetal Bovine Serum (Qualified, heat inactivated, Gibco Cat. # 16140-063). The medium is removed by aspiration and the cells washed with 10 mL of Hank's Balanced Salt solution (Gibco Cat. # 14175-095). The salt solution is removed by aspiration and the cells trypsinized with 5 mL of trypsin-EDTA (0.05% trypsin, 0.53 mM EDTA-4Na, Gibco Cat. # 25300-070) for 1 min. The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 day interval (or as appropriate). The cells grow to confluency (approx. >75%–95%) within 7–8 days. All steps are done under sterile conditions.

B. Membrane Preparation:

The cells are washed twice gently with Hank's Balanced Salt solution (e.g. use 10 mL per T-150 flask). The excess solution is removed and the cells bathed for 15–30 min. in an enzyme-free Cell Dissociation Buffer (e.g. use 8 mL Hank's Based, Gibco Cat. # 13150-016 per T-150 flask) until cells are loosened. The contents are transferred to centrifuge tubes (50 mL) kept in an ice bath. All subsequent steps are done at 4° C. The tubes are centrifuged at 300×g for 15 min (1380 rpm on SORVAL, Model RT6000D, using the rotor for 50 mL tubes). The supernatant is discarded and the cells suspended in homogeneizing buffer(10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with Polytron at setting 6 for 10 sec. The homogenate is transferred into a Potter-Elvjehm homogeneizer and homogenized with 3 strokes. The homogenate is centrifuged at 1500×g for 60 min at 4° C. (3100 rpm using SORVAL, model RT6000D, using the rotor for 50 mL tubes). The pellet is discarded. The supernatant is centrifuged at 100,000×g for 60 min. at 4° C. (Beckman L8–80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1% BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 μL of unlabeled arginine vasopressin (AVP) (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For vasopressin and other peptide ligands 20 μL of 50% DMSO is added and the assay buffer volume is adjusted accordingly.

To each well is added 50 μL of frozen membrane suspension thawed immediately prior to use and diluted in assay buffer to the required concentration (equivalent to 25 to 50 μg of protein/well as needed). 20 μL of 8 nM [$^3$H]arginine vasopressin ligand in the assay buffer, prepared just before use is added and incubated at room temperature for 60 min. shaking the plate on a mechanical shaker for the first 15 min. The incubation is stopped by rapid filtration of the plate contents followed by wash with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Oxytocin binding in Chinese Hamster Ovary cell membranes expressing human oxytocin receptors Receptor Source:

Chinese Hamster Ovary (CHO) cells stably transfected with the human oxytocin (cf. Tanizawa et al., U.S. Pat. No. 5,466,584 (1995) to Rohto Pharmaceutical Co. Ltd., Osaka, Japan) were obtained from M. Thibonnier, Case Western Reserve University School of Medicine, Cleveland, Ohio.

A. Passaging and Amplification of Cells:

CHO cells transfected with the human oxytocin receptors obtained from M. Thibonnier (pcDNA3.1 vector) are allowed to grow to confluency (approx. >90%) in T-150 flasks under sterile conditions, in a cell culture medium consisting of F-12 Nutrient Mixture (HAM) with L-glutamine (Gibco Cat. # 11765-054) containing 15 mM HEPES (Gibco Cat. # 15630-080), 1% antibiotic/antimycotic (add 5 mL 100×, Gibco Cat. # 15240-062 per 500 mL F-12), 400 μg/mL of Geneticin (add 4 mL of 50 mg/mL per 500 mL F-12) and 10% Fetal Bovine Serum (Qualified, heat inactivated, Gibco Cat. # 16140-063). The medium is removed by aspiration and the cells are washed with 10 mL of Hank's Balanced Salt solution (Gibco Cat. # 14175-095). The salt solution is removed by aspiration and the cells trypsinized with 5 mL of trypsin-EDTA (0.05% trypsin, 0.53 mM EDTA-4Na, Gibco Cat. # 25300-070) for 1 min The trypsin is removed by aspiration and the cells dislodged by tapping. Cell Culture medium (e.g. 30 mL for 1:30 split) is immediately added and mixed well to inactivate trypsin. 1 mL of detached cells is added to new culture flasks containing fresh Cell Culture medium (e.g. into 25 mL per T-150 flask), and mixed gently. The cells are incubated at 37° C. in 5% $CO_2$. The medium is changed at 3 to 4 days interval (or as appropriate). The cells grow to confluency (approx. >75%–95%) within 7–8 days. All steps are done under sterile conditions.

B. Membrane Preparation:

The cells are washed twice gently with Hank's Balanced Salt solution (eg, use 10 mL per T-150 flask). The excess solution is removed and the cells bathed for 15–30 min. in an enzyme-free Cell Dissociation Buffer (eg, use 8 mL Hank's Based, Gibco Cat. # 13150-016 per T-150 flask) until cells are loosened. The contents are transferred to centrifuge tubes (50 mL size) kept in ice bath. All subsequent steps are done at 4° C. The tubes are centrifuged at 300×g for 15 min (1380 rpm on SORVAL, Model RT6000D, using rotor for 50 mL tubes). The supernatant is discarded and the cells suspended in homogenizing buffer (10 mM Tris-HCl containing 0.25 M sucrose and 1 mM EDTA, pH 7.4) ensuring that the volume of the buffer is about ten times the volume of the cell pellet. The cells are pooled into a centrifuge tube (50 mL) and homogenized with a Polytron at setting 6 for 10 sec. The homogenate is transferred into a Potter-Elvjehm homogenizer and homogenized with 3 strokes. The homogenate is centrifuged at 1500×g for 10 min at 4° C. (3100 rpm using SORVAL, model RT6000D, using rotor for 50 mL tubes). The pellet is discarded. The supernatant is centrifuged at 100,000×g for 60 min. at 4° C. (Beckman L8-80M ultracentrifuge; spin at 37,500 rpm with rotor type 70 Ti for 50 mL tubes; 38,000 rpm with type 80Ti for 15 mL tubes; or 35,800 rpm with rotor type 45Ti). The supernatant is discarded and the pellet suspended in 3 to 4 mL of Tris buffer (50 mM TRIS-HCl, pH 7.4). The protein content is estimated by the Bradford or Lowry method. The volume of the membrane suspension is adjusted with the membrane buffer (50 mM Tris-HCl containing 0.1 % BSA and 0.1 mM PMSF) to give 3.0 mg/mL (or as appropriate) of protein. The membranes are aliquoted and stored at −70° C.

C. Radioligand Binding Assay:

In wells of a 96-well format microtiter plate, is added 90, 110 or 130 μL (to make up a final volume of 200 μL) of assay buffer containing 50 mM of Tris-HCl (pH 7.4), BSA (heat inactivated, protease-free), 5 mM of 0.1% $MgCl_2$, 1 mg % aprotinin, 1 mg % leupeptin, 2 mg % 1,10-phenanthroline, 10 mg % trypsin inhibitor, and 0.1 mM PMSF. The inhibitors are added on the day of the experiment. The components are mixed at room temperature, and then kept in ice bath following adjustment of the pH to 7.4. To each well is added 20 μL of unlabeled oxytocin (to give a final concentration of 0.1 to 10 nM for standard curve and 1000 nM for non specific binding) or test compounds in 50% DMSO (e.g. for final concentrations of 0.1 to 1000 nM or as appropriate) or 50% DMSO as vehicle control. For oxytocin and other peptide ligands, 20 μL of 50% DMSO is added and the assay buffer volume is adjusted accordingly.

To each well is added 50 μL of frozen membrane suspension thawed immediately prior to use and diluted in assay buffer to the required concentration (equivalent to 25 to 50 μg of protein/well as needed). 20 μL of 8 nM [$^3$H]oxytocin in the assay buffer, prepared just before use is added and incubated at room temperature for 60 min. shaking the plate on a mechanical shaker for the first 15 min. The incubation is stopped by rapid filtration of the plate contents followed by washing with ice-cold buffer (50 mM Tris-HCl, pH 7.4) using a cell harvester (Tomtek and Printed filtermat-B filter paper). The filter paper is thoroughly dried (7–12 min. in a microwave oven) and impregnated with MeltiLex B/H melt-on scintillation wax sheets and the radioactivity counted in a betaplate scintillation counter.

Binding data is either reported as percent inhibition at a certain concentration or if an $IC_{50}$ was calculated, as a nanomolar concentration. The results of these tests on representative compounds of this invention are shown in Table I.

TABLE 1

Binding to membranes of Chinese Hamster Ovary (CHO) cell line stably transfected with human vasopressin $V_{1a}$ receptor subtype, human vasopressin $V_2$ receptor subtype and human oxytocin receptor

| Example | OT % inhibition @ 100 nM ($IC_{50}$, nM)* | $V_{1a}$ % inhibition @ 100 nM ($IC_{50}$, nM)* | $V_2$ % inhibition @ 100 nM ($IC_{50}$, nM) |
|---|---|---|---|
| 1 | (4.47) | (1086) | (1188) |
| 2 | (3.17) | (1318) | (1420) |
| 3 | 96 | 41 | 7 |
| 4 | 99 | 61 | 20 |
| 5 | 34 | 18 | 12 |
| 6 | 31 | 6 | 3 |
| 7 | 42 | 13 | 6 |
| 8 | 84 | 43 | 16 |
| 9 | 37 | 5 | 21 |
| 10 | 45 | 13 | 15 |
| 11 | 87 | 54 | 17 |
| 12 | 98 | 73 | 21 |
| 13 | 95 | 51 | 12 |

*Binding in Chinese Hamster Ovary cell membranes expressing human vasopressin $V_{1a}$ and $V_2$ subtype receptors and human oxytocin receptors The following examples are presented to illustrate rather than limit the scope of this invention.

EXAMPLE 1

10-(5-Chloro-4-cyclohex-1-en-1-yl-2-methoxybenzoyl)-N-methyl-N-(pyridin-3-ylmethyl)-10,11-dihydro-5H-pyrrolo [2,1-c][1,4] benzodiazepine-3-carboxamide Step A. 4-Amino-5-chloro-2-methoxy-benzoic acid methyl ester 4-Amino-5-chloro-2-methoxy benzoic acid (50.0 g, 248 mmol) was suspended in methanol (500 mL) and the slurry cooled to 0° C. Thionyl chloride (54.3 mL, 744 mmol) was then added dropwise over the course of 20 minutes. Initially, a clear solution formed, which subsequently turned to a white suspension. The reaction was warmed to room temperature and stirred for 3 hours. The methanol was evaporated and the resulting slurry suspended in diethyl ether (1 L). The solid was filtered and rinsed thoroughly with diethyl ether to afford the title compound (50.9 g) as the hydrochloride salt. The salt was suspended in 1 N aqueous NaOH and stirred vigorously for 30 minutes. Filtration and thorough rinsing with water afforded the title compound free base as a white solid, m.p. 136–137° C.

$^1$H NMR (DMSO-d$_6$, 400 MHz): δ 7.57 (s, 1H), 6.43 (s, 1H), 6.14 (s, 2H), 3.71 (s, 3H), 3.67 (s, 3H). Anal. Calcd. for C₉H₁₀ClNO₃: C 50.13, H 4.67, N 6.50. Found: C 49.85, H 4.46, N 6.65. MS [(+)-APCl, m/z]: 216 [M+H⁺. Calcd. for C₉H₁₁ClNO₃: 216.0428.

Step B. 5-Chloro-4-iodo-2-methoxy-benzoic acid methyl ester

4-Amino-5-chloro-2-methoxy benzoic acid methyl ester of Step A (5.00 g, 23.2 mmol) was suspended in water (52 mL) and concentrated sulfuric acid (13 mL) was added. The resulting suspension was cooled to −1° C. and a solution of sodium nitrite (1.76 g, 25.5 mmol) in water (10 mL) was added at a rate which maintained the temperature below 0° C., resulting in the formation of a clear yellow solution. A mixture of potassium iodide (4.23 g, 25.5 mmol) and iodine (3.24 g, 12.8 mmol) in water (50 mL) was then added dropwise and the reaction stirred at 0° C. for 1.5 hours. The reaction mixture was warmed to room temperature and extracted with ethyl acetate (200 mL). The combined extracts were washed sequentially with 1 M aqueous sodium thiosulfate, 1 N sodium hydroxide and brine, and dried over anhydrous magnesium sulfate, filtered and concentrated, whereupon the product crystallized. The resulting orange crystals were suspended in petroleum ether, filtered and dried in vacuo to provide the title compound (6.38 g), m.p. 72–73° C.

¹H NMR (DMSO-d₆, 400 MHz): δ 7.72 (s, 1H), 7.66 (s, 1H), 3.83 (s, 3H), 3.77 (s, 3H). Anal. Calcd. for C₉H₈ClIO₃: C 33.11, H 2.47. Found: C 33.21, H 2.23. MS [(+)-APCl, m/z]: 327 [M]⁺. Calcd. for C₉H₉ClIO₃: 326.9285.

Step C. 5-Chloro-4-iodo-2-methoxy-benzoic acid

A mixture of 5-chloro-4-iodo-2-methoxy benzoic acid methyl ester of Step B (3.00 g, 9.19 mmol) and sodium hydroxide (1.10 g, 27.6 mmol) in methanol (92 mL) was refluxed for 12 hours. The reaction was cooled to room temperature and the solvent evaporated. The residue was dissolved in 1 N sodium hydroxide (75 mL), the solution washed with diethyl ether and the organic washings discarded. The aqueous phase was acidified with 2 N HCl and extracted with diethyl ether. The combined extracts were dried over anhydrous sodium sulfate, filtered and concentrated to afford the title carboxylic acid (2.64 g) as orange crystals, m.p. 150–151° C.

¹H NMR (DMSO-d₆, 400 MHz): δ 13.03 (bs, 1H), 7.70 (s, 1H), 7.63 (s, 1H), 3.82 (s, 3H). Anal. Calcd. for C₈H₆ClIO₃: C 30.75, H 1.94. Found: C 31.28, H 1.78. MS [(−)-APCl, m/z]: 311 [M—H⁻]. Calcd. for C₈H₅ClIO₃: 310.8972.

Step D. (10,11-Dihydro-5H-pyrrolo[2,1 -c][1,4] benzodiazepin-10-yl)-(2-methoxy-4-iodo-5-chlorophenyl)-methanone To a mixture of 5-chloro-4-iodo-2-methoxy benzoic acid of Step C (0.900 g, 2.88 mmol) and N,N-dimethylformamide (6.7 μL, 86.4 μmol) in anhydrous dichloromethane (14.4 mL) was added dropwise oxalyl chloride (0.263 mL, 3.02 mmol). The mixture was heated to reflux for 1 hour, then cooled to room temperature and evaporated to dryness. Fresh anhydrous dichloromethane (25 mL) was added, the resulting solution was concentrated and the residue dried in vacuo. The crude acid chloride thus obtained and 10,11-dihydro-5H-pyrrolo[2,1-c][1,4] benzodiazepine (0.584 g, 3.17 mmol) were combined in anhydrous dichloromethane (14.4 mL), followed by addition of N,N-diisopropylethyl amine (0.447 mL, 3.46 mmol). After stirring at room temperature for 18 hours, the reaction mixture was diluted with dichloromethane (15 mL) and washed sequentially with 1 N hydrochloric acid, 1 N sodium hydroxide, and brine. The organic phase was dried over anhydrous magnesium sulfate, filtered and concentrated to afford the crude title amide which was recrystallized from diethyl ether to provide 1.23 g of slightly orange crystals, m.p. 191–192° C.

¹H NMR (DMSO-d₆, 400 MHz): δ 7.60–7.28 (m, 3H), 7.14–7.01 (m, 3H), 6.79 (s, 1H), 5.95 (s, 1H), 5.89 (t, J=3.1, 1H), 5.15 (bs, 4H), 3.56 (s, 3H). Anal. Calcd. for C₂₀H₁₆ClIN₂O₂: C 50.18, H 3.37, N 5.85. Found: C 50.47, H 3.28, N 5.74. MS (EI, m/z): 478 [M]⁺. Calcd. for C₂₀H₁₆ClIN₂O₂: 477.9946.

Step E. (10,11-Dihydro-5H-pyrrolo[2,1-c][1,4]benzodiazepin-10-yl)-[5-chloro-2-methoxy-4-(4,4,5,5-tetramethyl-[1,3,2]dioxaborolan-2-yl)-phenyl]-methanone (10,11-Dihydro-5H-pyrrolo[2,1-c][1,4]benzodiazepin-10-yl)-(2-methoxy-4-iodo-5-chlorophenyl)-methanone of Step D (0.500 g, 1.04 mmol), bis(pinacolato)diboron (0.289 g, 1.14 mmol), potassium acetate (0.306 g, 3.12 mmol) and dichloro[1,1'-bis(diphenylphosphino) ferrocene]palladium (II) dichloromethane adduct (0.025 g, 0.0312 mmol) were combined in anhydrous dimethyl sulfoxide (5.2 mL) and heated to 80° C. overnight. The reaction mixture was cooled to room temperature, diluted with ethyl acetate and washed with water and brine. The organic phase was dried over anhydrous sodium sulfate, diluted with hexane and filtered through a plug of silica gel. The filtrate was concentrated to an oil which crystallized from diethyl ether/petroleum ether (−20° C.). to provide the title compound (0.430 g) as a white, crystalline solid, m.p. 92–98° C.

¹H NMR (DMSO-d₆, 400 MHz): δ 7.48–7.36 (m, 2H), 7.12–7.03 (m, 4H), 6.79 (s, 1H), 5.95 (m, 1H), 5.89 (t, 1H), 5.20 (br, 4H), 3.48 (br, 3H), 1.26 (s, 12H). Anal. Calcd. for C₂₆H₂₈BClN₂O₄: C 56.22, H 5.89, N 5.85. Found: C 56.23, H 5.63, N 6.24. MS [(+)-ESI, m/z]: 479 [M+H]⁺. Calcd. for C₂₆H₂₉BClN₂O₄: 479.1910.

Step F. 10-(5-Chloro-4-cyclohex-1-en-1-yl-2-methoxybenzoyl)-10,11 -dihydro-5H-pyrrolo[2,1-c][1,4]benzodiazepine (10,11-Dihydro-5H-pyrrolo[2,1-c][1,4]benzodiazepin-10-yl)-[5-chloro-2-methoxy-4-(4,4,5,5-tetramethyl-[1,3,2] dioxaborolan-2-yl)-phenyl]-methanone of Step E (0.220 g, 0.459 mmol), cyclohex-1-en-1-yl trifluoromethanesulfonate (0.116 g, 0.505 mmol) and dichloro[1,1'-bis (diphenylphosphino)ferrocene]palladium (II) dichloromethane adduct (0.0110 g, 0.0138 mmol) were combined in N,N-dimethyl formamide (2.3 mL). Aqueous sodium carbonate (2 M, 1.15 mL, 2.30 mmol) was added and the reaction heated to 60° C. for 2 hours. After cooling to room temperature, the reaction mixture was diluted with ethyl acetate (50 mL) and washed with water and brine. The organic phase was dried over anhydrous magnesium sulfate, filtered and concentrated. Flash column chromatography on silica gel using a solvent gradient from 30 to 40% ethyl acetate in hexane afforded the title compound (0.140 g) as an oil. The oil was dissolved in diethyl ether/petroleum ether and concentrated to afford an amorphous white solid.

¹H NMR (DMSO-d₆, 400 MHz): δ 7.38 (d, 2H), 7.11 (t, 1H), 7.06–7.00 (m, 2H), 6.79 (s, 1H), 6.57 (s, 1H), 5.95 (s, 1H), 5.89 (t, 1H), 5.55 (s, 1H), 5.24–4.60 (m, 4H), 3.52 (s, 3H), 2.13–2.09 (m, 4H), 1.68–1.57 (m, 4H). Anal. Calcd. for C₂₆H₂₅ClN₂O₂+0.03 C₄H₁₀O: C 71.76, H 5.79, N 6.44. Found: C 71.66, H 5.59, N 6.10. MS [(+)-APCl, m/z]: 433 [M+H]⁺. Calcd. for C₂₆H₂₆ClN₂O₂: 433.1684.

Step G. 10-(5-Chloro-4-cyclohex-1-en-1-yl-2-methoxybenzoyl)-10,11-dihydro-5H-pyrrolo[2,1-c][1,4]benzodiazepine-3-carboxylic acid 10-(5-Chloro-4-cyclohex-1-en-1-yl-2-methoxybenzoyl)-10,11-dihydro-5H-pyrrolo[2,1-c][1,4]benzodiazepine of Step F (0.300 g, 0.693 mmol) and N,N-diisopropylethyl amine (0.127 mL, 0.728 mmol) were dissolved in anhydrous dichloromethane (2.8 mL). Trichloroacetyl chloride (0.116 mL, 1.04 mmol) was added dropwise and the reaction stirred at room temperature for 3 hours. The mixture was diluted with ethyl acetate and washed with 1 N HCl, 1 N NaOH and brine. The organic phase was dried over anhydrous magnesium sulfate, diluted with hexane and stirred at room temperature for 4 hours, then diluted with 1 N hydrochloric acid (50 mL) and extracted with diethyl ether. The organic phase was extracted with 1 N sodium filtered through silica gel using 30% ethyl acetate in hexane. Concentration of the filtrate afforded crude trichloroacetate (0.360 g). This material was dissolved in acetone (4.2 mL) and 2.5 N sodium hydroxide (0.750 mL) added. The reaction was hydroxide and the combined basic extracts acidified with 2 N hydrochloric acid. The aqueous phase was extracted with diethyl ether and the extract dried over anhydrous sodium sulfate, filtered and concentrated to afford the title compound (0.280 g) as a white solid, m.p. 192° C. (dec.).

$^1$H NMR (DMSO-$d_6$, 400 MHz): δ 12.34 (br, 1H), 7.42 (br, 1H), 7.25 (d, 1H), 7.07 (t, 1H), 6.98 (t, 1H), 6.93 (d, 1H), 6.72 (d, 1H), 6.54 (br, 1H), 6.10 (d, 1H), 5.90–4.60) (m, 5H), 3.47 (br, 3H), 2.14–2.09 (m, 4H), 1.65–1.57 (m, 4H). Anal. Calcd. for $C_{27}H_{25}ClN_2O_4$: C 67.99, H 5.28, N 5.87. Found: C 67.71, H 5.23, N 5.49. MS [(−)-APCl, m/z]: 475 [M-H]$^-$. Calcd. for $C_{27}H_{24}ClN_2O_4$: 475.1426.

Step H. 10-(5-Chloro-4-cyclohex-1-en-1-yl-2-methoxybenzoyl)-N-methyl-N-(pyridin-3-ylmethyl)-10,11-dihydro-5H-pyrrolo [2,1-c][1,4]benzodiazepine-3-carboxamide 10-(5-chloro-4-cyclohex-1-en-1-yl-2-methoxybenzoyl)-10,11-dihydro-5H-pyrrolo[2,1-c][1,4]benzodiazepine-3-carboxylic acid of Step G (0.125 g, 0.262 mmol), 3-(methylaminomethyl)pyridine (0.038 g, 0.314 mmol), 1-hydroxy benzotriazole (0.039 g, 0.288 mmol) and 1-[(3-dimethylamino)propyl]-3-ethylcarbodiimide hydrochloride (0.055 g, 0.288 mmol) were combined in amine-free N,N-dimethylformamide (1.1 mL), followed by addition of N,N-diisopropylethyl amine (0.068 mL, 0.393 mmol). The reaction was stirred at room temperature for 16 hours, then diluted with ethyl acetate and washed with water, saturated aqueous sodium bicarbonate and brine. The combined aqueous washings were saturated with sodium chloride and extracted with ethyl acetate. The combined organic phases were dried over anhydrous magnesium sulfate, filtered and concentrated. The residue was purified by flash column chromatography on silica gel eluting with 5% methanol in chloroform, and recrystallized from diethyl ether/pentane to afford 0.140 g of the title compound as a white crystalline solid, m.p. 178–179° C., 98.0% pure by analytical HPLC (Primesphere C-18, 2.0×150 mm, 45% acetonitrile/water, 0.2 mL/min.).

$^1$H NMR (DMSO-$d_6$, 400 MHz): δ 8.53–8.50 (m, 2H), 7.71 (d, 1H), 7.45–7.41 (m, 2H), 7.31 (d, 1H), 7.08 (t, 1H), 6.98 (t, 1H), 6.94 (d, 1H), 6.54 (s, 1H), 6.33 (s, 1H), 6.05 (d, 1H), 5.56 (s, 1H), 5.37 (s, 2H), 5.35–4.80 (br, 2H), 4.74 (s, 2H), 3.48 (br, 3H), 3.03 (s, 3H), 2.14–2.09 (m, 4H), 1.65–1.57 (m, 4H). Anal. Calcd. for $C_{34}H_{33}ClN_4O_3$: C 70.27, H 5.72, N 9.64. Found: C 69.95, H 5.77, N 9.31. MS [(+)-APCl, m/z]: 581.0 [M+H]$^+$. Calcd. for $C_{34}H_{34}ClN_4O_3$ 581.2321.

EXAMPLE 2

10-(5-Chloro-4-cyclohex-1-en-1-yl-2-methoxybenzoyl)-N-methyl-N-(pyridin-3-ylmethyl)-10,11-dihydro-5H-pyrrolo[2,1- c][1,4] benzodiazepine-3-carboxamide L-(+)-tartaric acid salt hemihydrate 10-(5-Chloro-4-cyclohex-1-en-1-yl-2-methoxybenzoyl)-N-methyl-N-(pyridin-3-ylmethyl)-10,11-dihydro-5H-pyrrolo[2,1- c][1,4]benzodiazepine-3-carboxamide of Example 1 (0.200 g, 0.344 mmol), was dissolved in boiling diethyl ether. A solution of L-(+)-tartaric acid (0.0520 g, 0.344 mmol) in hot methanol (1 mL) was added, the mixture cooled and solvent evaporated. Diethyl ether was added to the residue causing a white solid to form which was filtered and dried in vacuo to provide 0.252 g of the title compound tartaric acid salt, m.p. 138–177° C.

$^1$H NMR (DMSO-$d_6$, 400 MHz): δ 12.66 (br, 2H), 8.53–8.50 (m, 2H), 7.71 (d, 1H), 7.43–7.40 (m, 2H), 7.31 (d, 1H), 7.08 (t, 1H), 6.98 (t, 1H), 6.93 (d, 1H), 6.54 (s, 1H), 6.33 (s, 1H), 6.05 (d, 1H), 5.57 (s, 1H), 5.37 (s, 2H), 5.35–4.80 (br, 4H), 4.74 (s, 2H), 4.30 (s, 2H), 3.48 (br, 3H), 3.03 (s, 3H), 2.14–2.09 (m, 4H), 1.65–1.57 (m, 4H). Anal. Calcd. for $C_{34}H_{33}ClN_4O_3$+1.00 $C_4H_6O_6$+0.50 $H_2O$: C 61.66, H 5.45, N 7.57 Found: C 61.73, H 5.44, N 7.17. MS [EI, m/z]: 580 [M]$^+$. Calcd. for $C_{34}H_{33}ClN_4O_3$ 580.2243.

EXAMPLE 3

10-[4-((3R)-3-Hydroxy-2-methyl-cyclohex-1-en-1-yl)-3-methyl-benzoyl]-10,11-dihydro-5H-pyrrolo[2, 1-c][1,4]benzodiazepine-3-carboxylic acid methyl-pyridin-3-yl methyl-amide Step A. (10,1-Dihydro-5H-pyrrolo [2,1q-c][1,4] benzodiazepin-10-yl)-[(3-oxo-2-methyl-cyclohex-1-en-1-yl)-3-methyl-phenyl] methanone (10,11-Dihydro-5H-pyrrolo[2,1-c][1,4]benzodiazepin-10-yl)-[3-methyl-4-(4,4,5,5-tetramethyl-[1,3,2] dioxaborolan-2-yl)-phenyl]-methanone of Example 5 Step B (6.75 g, 15.8 mmol), 3-oxo-2-methylcyclohex-1-en-1-yl trifluoromethanesulfonate (4.49 g, 17.4 mmol) and dichloro[1,1'-bis(diphenylphosphino)ferrocene]palladium (II) dichloromethane adduct (0.387 g, 0.474 mmol) were combined in dimethyl sulfoxide (79 mL). Aqueous sodium carbonate (2 M, 39.5 mL, 79.0 mmol) was added and the reaction heated to 60° C. for 3 hours. After cooling to room temperature, the reaction mixture was diluted with water and washed with ethyl acetate. The combined extracts were washed with water and brine. The organic phase was dried over anhydrous sodium sulfate, filtered through silica gel and concentrated. The residue was purified by flash column chromatography on silica gel eluting with 50% ethyl acetate in hexane to provide 3.55 g of the title compound as a pale orange foam.

$^1$H NMR (DMSO-$d_6$, 400 MHz): δ 7.45 (dd, 1H), 7.24 (s, 1H), 7.17 (t, 1H), 7.07 (t, 1H), 7.05 (d, 1H), 6.91 (d, 1H), 6.85 (d, 1H), 6.82 (t, 1H), 5.94 (s, 1H), 5.91 (t, 1H), 5.34–4.65 (br, 4H), 2.42–2.32 (m, 4H), 2.02 (s, 3H), 2.00–1.93 (m, 2H), 1.25 (s, 3H). Anal. Calcd. for $C_{27}H_{26}N_2O_2$+0.50 $H_2O$+0.05 $C_6H_{14}$: C 77.37, H 6.59, N 6.60. Found: C 77.40, H 6.76, N 6.51. MS [(+)-APCl, m/z]: 411.1 [M+H]$^+$. Calcd. for $C_{27}H_{27}N_2O_2$: 411.2078.

Step B. (10,11-Dihydro-5H-pyrrolo[2,1-c][1,4] benzodiazepin-10-yl)-[4-((3R)-3-hydroxy-2-methyl-cyclohex-1-en-1-yl)-3-methyl-phenyl]-methanone (S)-(−)-tetrahydro-1-methyl-3,3-diphenyl-1H,3H-pyrrolo [1,2-c][1,3,2]oxazaborole [(S)-(−)-CBS-oxazaborolidine] (1.0 M in THF, 1.06 mL, 1.06 mmol) was dissolved in anhydrous tetrahydrofuran (53.1 mL, distilled from sodium/benzophenone ketyl). To this solution was simultaneously added a solution of (10,1-dihydro-5H-pyrrolo [2,1q-c][1,4] benzodiazepin-10-yl)-[(3-oxo-2-methyl-cyclohex-1-en-1-yl)-3-methyl-phenyl]methanone of Step A (2.18 g, 5.31 mmol) in anhydrous tetrahydrofuran (20 mL) via syringe pump (1.6 mL/min) and borane-tetrahydrofuran complex (1.0 M in tetrahydrofuran, 3.19 mL, 3.19 mmol) at a rate such that enone addition was complete upon addition of approximately ⅔ of the borane-tetrahydrofuran complex. Upon completion of the borane-tetrahydrofuran complex addition, the reaction mixture was diluted with water and extracted with ethyl acetate. The combined extracts were washed with 1 N sodium hydroxide, 1 N hydrochloric acid and brine, and dried over anhydrous magnesium sulfate, filtered and concentrated. The residue was purified by flash column chromatography on silica gel eluting with 50% ethyl acetate in hexane followed by precipitation from diethyl ether upon addition of petroleum ether, to afford 2.02 g of the title compound as a white solid. Analytical HPLC (Chiralpak AD, 4.6×250 mm, 50% ethanol/hexane, 0.5 mL/min.) indicated an enantiomeric excess of 96.4%, $[\alpha]_{589}$=+34.30 (c=1.0, chloroform).

$^1$H NMR (DMSO-$d_6$, 400 MHz): δ 7.45 (dd, 1H), 7.18–7.14 (m, 2H), 7.07 (t,1H), 6.95 (t, 1H), 6.88 (d, 1H), 6.81 (t, 1H), 6.73 (t, 1H), 5.93 (s, 1H), 5.91 (t, 1H), 5.27 (br, 2H), 5.25–4.80 (br, 2H), 3.90–3.84 (m, 1H), 1.99 (d, 3H), 1.90 (br, 2H), 1.75–1.59 (m, 3H), 1.54–1.49 (m, 1H), 1.24 (s, 3H). Anal. Calcd. for $C_{27}H_{28}N_2O_2$+0.50 $H_2O$+0.10 $C_4H_{10}O$: C 75.60, H 6.81, N 6.53. Found: C 75.52, H 6.92, N 6.54. MS [(+)-APCl, m/z]: 413.2 [M+H]$^+$. Calcd. for $C_{27}H_{29}N_2O_2$: 413.2230.

Step C. 10-[4-((3R)-3-hydroxy-2-methyl-cyclohex-1-en-1-yl)-3-methyl-benzoyl]-10,11-dihydro-5H-pyrrolo[2,1-c][1,4]benzodiazepine-3-carboxylic acid (10,11-Dihydro-5H-pyrrolo[2,1-c][1,4]benzodiazepin-10-yl)-[4-((3R)-3-hydroxy-2-methyl-cyclohex-1-en-1-yl)-3-methyl-phenyl]-methanone of Step B (0.500 g, 1.21 mmol), and N,N-diisopropylethyl amine (0.442 mL, 2.54 mmol) were dissolved in anhydrous dichloromethane (12.1 mL). Trichloroacetyl chloride (0.297 mL, 2.66 mmol) was then added dropwise and the reaction was stirred at room temperature for 3.5 hours, diluted with ethyl acetate and washed with 1 N hydrochloric acid, saturated aqueous sodium bicarbonate and brine. The organic phase was dried over anhydrous sodium sulfate, filtered and concentrated. The residue was filtered through a plug of silica gel eluting with 30% ethyl acetate in hexane, and the filtrate was concentrated to afford the crude bis-trichloroacetate as a brown foam. This material was dissolved in acetone (8.1 mL) and treated with 2.5 N sodium hydroxide (1.94 mL, 4.84 mmol). After stirring at room temperature for 2.5 hours, the reaction mixture was acidified with 1 N hydrochloric acid (50 mL) and extracted with diethyl ether. The combined organic extracts were extracted with 1 N sodium hydroxide and the basic extracts combined and acidified with 2 N hydrochloric acid. Upon acidification, a precipitate formed which was filtered and dried to afford 0.510 g of the title compound as a brown solid, $[\alpha]_{589}$=+17.84 (c=1.0, chloroform).

$^1$H NMR (DMSO-$d_6$, 400 MHz): δ 12.33 (br, 1H), 7.33 (dd, 1H), 7.14–7.11 (m, 2H), 7.02 (t, 1H), 6.94 (t, 1H), 6.82 (d, 1H), 6.76–6.71 (m, 2H), 6.09 (d, 1H), 6.04–5.76 (br, 2H), 5.44–4.90 (br, 2H), 4.63 (t, 1H), 3.89–3.83 (m, 1H), 1.99 (dd, 3H), 1.90 (br, 2H), 1.72–1.59 (m, 3H), 1.53–1.49 (m, 1H), 1.25 (s, 3H). Anal. Calcd. for $C_{28}H_{28}N_2O_4$: C 73.66, H 6.18, N 6.14. Found: C 66.75, H 5.97, N 5.04. MS [(−)-ESI m/z]: 455.4 [M−H]$^−$. Calcd. for $C_{28}H_{27}N_2O_4$: 455.1972.

Step D. 10-[4-((3R)-3-Hydroxy-2-methyl-cyclohex-1-en-1-yl)-3-methyl-benzoyl]-10,11-dihydro-5H-pyrrolo[2,1-c][1,4]benzodiazepine-3-carboxylic acid methyl-pyridin-3-yl methyl-amide 10-[4-((3R)-3-hydroxy-2-methyl-cyclohex-1-en-1-yl)-3-methyl-benzoyl]-10,11-dihydro-5H-pyrrolo[2,1-c][1,4]benzodiazepine-3-carboxylic acid of Step C (0.250 g, 0.548 mmol), 3-(methylaminomethyl)pyridine (0.080 mL, 0.658 mmol), 1-hydroxy benzotriazole (0.081 g, 0.603 mmol) and 1-[(3-dimethylamino)propyl]-3-ethylcarbodiimide hydrochloride (0.116 g, 0.603 mmol) were combined in amine-free N,N-dimethylformamide (2.2 mL), followed by addition of N,N-diisopropylethyl amine (0.143 mL, 0.822 mmol). The reaction was stirred at room temperature for 18 hours, then diluted with ethyl acetate and washed with water, saturated aqueous sodium bicarbonate and brine. The combined aqueous washings were saturated with sodium chloride and extracted with ethyl acetate. The organic phases were combined, dried over anhydrous sodium sulfate, filtered and concentrated. The residue was purified by flash column chromatography on silica gel eluting with a solvent gradient from 0 to 8% of methanol in chloroform, to afford 0.270 g of the title compound as an oil which was dissolved in diethyl ether and precipitated with petroleum ether to afford a white solid, m.p.100–144° C., $[\alpha]_{589}$=+18.49 (c=1.0, chloroform).

$^1$H NMR (DMSO-$d_6$, 400 MHz): δ 8.54 (s, 1H), 8.51 (dd, 1H), 7.72 (d, 1H), 7.42 (dd, 1H), 7.37 (d, 1H), 7.15–7.11 (m, 2H), 7.02 (dt, 1H), 6.94 (t, 1H), 6.83 (d, 1H), 6.73 (t, 1H), 6.35 (br, 1H), 6.04 (d, 1H), 5.45 (s, 2H), 5.35–4.85 (br, 2H), 4.75 (s, 2H), 4.62 (t, 1H), 3.89–3.84 (m, 1H), 3.04 (s, 3H), 1.99 (d, 3H), 1.90 (br, 2H), 1.76–1.60 (m, 3H), 1.54–1.51 (m, 1H), 1.25 (s, 3H). Anal. Calcd. for $C_{35}H_{36}N_4O_3$+0.15 $C_4H_{10}O$: C 73.52, H 6.35, N 9.80. Found: C 73.68, H 6.67, N 9.42. MS [(+)-ESI, m/z]: 561.3 [M+H]$^+$. Calcd. for $C_{35}H_{37}N_4O_3$: 561.2867.

EXAMPLE 4

10-[4-((3R)-3-Hydroxy-2-methyl-cyclohex-1-en-1-yl)-3-methyl-benzoyl]-10,11-dihydro-5H-pyrrolo[2,1-c][1,4]benzodiazepine-3-carboxylic acid methyl-pyridin-3-yl methyl-amide L-(+)-tartaric acid salt 10-[4-((3R)-3-Hydroxy-2-methyl-cyclohex-1-en-1-yl)-3-methyl-benzoyl]-10,11-dihydro-5H-pyrrolo[2,1-c][1,4]benzodiazepine-3-carboxylic acid methyl-pyridin-3-yl methyl-amide (0.120 g, 0.214 mmol) of Example 3, was dissolved in boiling diethyl ether. A solution of L-(+)-tartaric acid (0.0320 g, 0.214 mmol) in hot methanol (1 mL) was added, the mixture cooled and solvent evaporated. Diethyl ether was added to the residue causing a white solid to form which was filtered and dried in vacuo to afford 0.152 g of the title compound as the tartaric acid salt.

$^1$H NMR (DMSO-$d_6$, 400 MHz): δ 12.67 (br, 2H), 8.54 (s, 1H), 8.51 (dd, 1H), 7.72 (d, 1H), 7.42 (dd, 1H), 7.37 (d, 1H), 7.13–7.11 (m, 2H), 7.02 (t, 1H), 6.94 (t, 1H), 6.83 (d, J1H), 6.73 (t, 1H), 6.35 (br, 1H), 6.05 (d, 1H), 5.46 (s, 2H), 5.07 (br, 4H), 4.75 (s, 2H), 4.63 (br, 1H), 4.30 (s, 2H), 3.86 (d, 1H), 3.04 (s, 3H), 1.99 (d, 3H), 1.90 (bs, 2H) 1.77–1.60 (m, 3H), 1.56–1.50 (m, 1H), 1.24 (s, 3H). Anal. Calcd. for $C_{35}H_{36}N_4O_3$+1.00 $C_4H_6O_6$+0.33 $C_4H_{10}O$: C 63.71, H 5.76, N7.62. Found: C 63.00, H 6.14, N 6.91. MS [(+)-ESI, m/z]: 561.2 [M+H]$^+$. Calcd. for $C_{35}H_{37}N_4O_3$: 561.2867.

EXAMPLE 5

10-[4-(1-Cyclohex-1-en-1-yl)-3-methylbenzoyl]-N-(2-pyridinylmethyl)-10,11-dihydro-5H-pyrrolo[2,1-c][1,4]benzodiazepine-3-carboxamide Step A. (10,11-Dihydro-5H-pyrrolo[2,1-c][1,4]benzodiazepin-10-yl)-(4-bromo-3-methyl-phenyl)-methanone To a stirred mixture of 4-bromo-3-methyl benzoic acid (21.5 g, 100 mmol) and N,N-dimethylformamide (0.251 mL, 3.00 mmol) in anhydrous dichloromethane (200 mL) was added dropwise oxalyl chloride (9.16 mL, 105 mmol). The mixture was heated to reflux for 1.5 hours, then cooled to room temperature and the solvent evaporated. Fresh anhydrous dichloromethane (200 mL) was added and the resulting solution concentrated and the residue was dried in vacuo. The crude acid chloride thus obtained and 10,11-dihydro-5H-pyrrolo [2,1-c][1,4]benzodiazepine (17.5 g, 95.0 mmol) were combined in anhydrous dichloromethane (200 mL), and N,N-diisopropylethylamine (19.2 mL, 110 mmol) was added. After stirring at room temperature for 18 hours, the reaction mixture was washed with 1 N hydrochloric acid, 1 N sodium hydroxide and brine. The organic phase was dried over anhydrous magnesium sulfate, filtered and concentrated to afford the crude amide which was recrystallized from ethyl acetate to provide pale orange crystals (34.8 g) of the title compound, m.p.175–176° C.

$^1$H NMR (DMSO-d$_6$, 400 MHz): δ 7.45 (dd, 1H), 7.38 (d, 1H), 7.33 (d, 1H), 7.18 (dt, 1H), 7.10 (t, 1H), 6.92 (s, 1H), 6.90 (s, 1H), 6.82 (t, 1H), 5.94 (s, 1H), 5.91 (t, 1H), 5.27–4.80 (br, 4H), 2.22 (s, 3H). Anal. Calcd. for C$_{20}$H$_{17}$BrN$_2$O+0.20 H$_2$O: C 62.42, H 4.56, N 7.28. Found: C 62.43, H 4.60, N 7.24. MS [(+)-ESI, m/z]: 381 [M+H]$_+$. Calcd. for C$_{20}$H$_{18}$BrN$_2$O: 381.0598.

Step B. (10,11-Dihydro-5H-pyrrolo [2,1-c][1,4] benzodiazepin-10-yl)-[3-methyl-4-(4,4,5,5-tetramethyl-[1,3,2]dioxaborolan-2-yl)-phenyl]- methanone (10,11 -Dihydro-5H-pyrrolo [2,1-c][1,4]benzodiazepin-10-yl)-(4-bromo-3-methyl-phenyl)-methanone of Step A (20.0 g, 52.5 mmol), bis(pinacolato)diboron (14.7 g, 57.8 mmol), potassium acetate (15.5 g, 158 mmol) and dichloro [1,1'-bis (diphenylphosphino) ferrocene]palladium (II) dichloromethane adduct (1.29 g,1.58 mmol) were combined in anhydrous dimethyl sulfoxide (263 mL) and heated to 80° C. for 18 hours. The reaction was cooled to room temperature and additional catalyst (1.29 g, 1.58 mmol) and bis (pinacolato)diboron (3.33 g, 13.1 mmol) were added. Heating was resumed at 80° C. for an additional 18 hours. The reaction mixture was cooled to room temperature, diluted with ethyl acetate (500 mL) and filtered through silica gel. The filtrate was washed with water and brine. The organic phase was dried over anhydrous sodium sulfate, diluted with hexane and filtered through a plug of silica gel. The filtrate was concentrated to an oil and pentane added, causing the product to crystallize. The off-white crystals were filtered and dried in vacuo to provide 18.4 g of the title compound, m.p.190–193° C.

$^1$H NMR (DMSO-d$_6$, 400 MHz): δ 7.45 (dd, 1H), 7.39 (d, 1H), 7.18–7.06 (m, 3H), 6.98 (d, 1H), 6.91 (br, 1H), 6.81 (t, 1H), 5.94 (br, 1H), 5.91 (t, 1H), 5.33–4.60 (br, 4H), 2.32 (s, 3H), 1.25 (s, 12H). Anal. Calcd for C$_{26}$H$_{29}$BN$_2$O$_3$+0.12 C$_4$H$_8$O$_2$: C 72.46, H 6.88, N 6.38. Found: C 70.80, H 6.83, N 6.06. MS [(+)-ESI, m/z]: 429 [M+H]$^+$. Calcd. for C$_{26}$H$_{30}$BN$_2$O$_3$: 429.2348.

Step C. (10,11-Dihydro-5H-pyrrolo [2,1-c][1,4] benzodiazepin-10-yl)-(4-cyclohex-1-en-1-yl-3-methyl-phenyl)-methanone (10,11-Dihydro-5H-pyrrolo [2,1-c][1,4]benzodiazepin-10-yl)-[3-methyl-4-(4,4,5,5-tetramethyl-[1,3,2] dioxaborolan-2-yl)-phenyl]-methanone of Step B (3.50 g, 8.17 mmol), cyclohex-1-en-1-yl trifluoromethanesulfonate (2.26 g, 9.80 mmol) and dichloro[1,1'-bis (diphenylphosphino)ferrocene]palladium (II) dichloromethane adduct (0.200 g, 0.245 mmol) were combined in N,N-dimethylformamide (40.9 mL). Aqueous sodium carbonate (2 M, 20.5 mL, 40.9 mmol) was added and the reaction heated to 60° C. overnight. After cooling to room temperature, the reaction mixture was diluted with ethyl acetate and the organic layer washed with water and brine. The organic phase was dried over anhydrous magnesium sulfate, filtered and concentrated. The residue was dissolved in hot ethyl acetate/petroleum ether (1:1) and filtered. The filtrate was concentrated and the residue recrystallized from petroleum ether to afford 2.52 g of the title compound as light brown crystals, m.p. 182–183° C.

$^1$H NMR (DMSO-d$_6$, 400 MHz): δ 7.47 (dd, 1H), 7.21–7.10 (m, 3H), 6.93 (d, 2H), 6.83 (d, 1H), 6.81 (t, 1H), 5.93–5.91 (m, 2H), 5.43 (m, 1H), 5.26 (br, 2H), 5.20–4.80 (br, 2H), 2.11 (s, 3H), 2.09–2.05 (m, 4H), 1.67–1.56 (m, 4H). Anal. Calcd. for C$_{26}$H$_{26}$N$_2$O+0.15 H$_2$O: C 81.07, H 6.88, N 7.27. Found: C 81.03, H 6.86, N 7.24. MS [(+)-ESI, m/z]: 383 [M+H]$^+$. Calcd. for C$_{26}$H$_{27}$N$_2$O: 383.2128.

Step D. 2,2,2-Trichloro-1-[10-(4-cyclohex-1-en-1-yl-3-methyl-benzoyl)-10,11-dihydro-5H-pyrrolo [2,1-c][1,4] benzodiazepin-3-yl]-methanone (10,11-Dihydro-5H-pyrrolo [2,1-c][1,4]benzodiazepin-10-yl)-(4-cyclohex-1-enyl-3-methyl-phenyl)-methanone of Step C (1.03 g, 2.69 mmol), and N,N-diisopropylethyl amine (0.937 mL, 5.38 mmol) were dissolved in anhydrous dichloromethane (13.5 mL) and trichloroacetyl chloride (0.901 mL, 8.07 mmol) added dropwise. The reaction was stirred at room temperature for 3 hours, and the solvent was evaporated. The residue was diluted with ethyl acetate and filtered through a plug of silica gel. The filtrate was washed with 0.1 N hydrochloric acid, saturated aqueous sodium bicarbonate, and brine, dried over anhydrous magnesium sulfate, filtered and concentrated. The residue was crystallized from ethyl acetate/hexane to afford 1.41 g of the title compound as white crystals, m.p. 149–150° C.

$^1$H NMR (DMSO-d$_6$, 400 MHz): δ 7.46–7.43 (m, 2H), 7.21–7.16 (m, 2H), 7.12 (dt, 1H), 6.95–6.90 (m, 2H), 6.85 (d, 1H), 6.34 (d, 1H), 5.95 (br, 2H), 5.44 (m, 1H) , 5.27 (br, 2H), 2.12 (s, 3H), 2.10–2.05 (m, 4H), 1.68–1.55 (m, 4H). Anal. Calcd. for C$_{28}$H$_{25}$Cl$_3$N$_2$O$_2$: C 63.71, H 4.77, N 5.31. Found: C 63.35, H 4.62, N 5.24. MS [(+)-ESI, m/z]: 527.2 [M+H]$^+$. Calcd. for C$_{28}$H$_{26}$Cl$_3$N$_2$O$_2$: 527.1058.

Step E. 10-(4-Cyclohex-1-en-1-yl-3-methyl-benzoyl)-10, 11-dihydro-5H-pyrrolo [2,1-c][1,4]benzodiazepine-3-carboxylic acid 2,2,2-Trichloro-1-[10-(4-cyclohex-1-en-1-yl-3-methyl-benzoyl)-10,11-dihydro-5H-pyrrolo [2,1-c][1,4] benzodiazepin-3-yl]-methanone of Step D (0.700 g, 1.33 mmol), was dissolved in acetone (8.9 mL) followed by addition of 2.5 N sodium hydroxide (1.60 mL, 3.99 mmol). The reaction was stirred at room temperature for 3 hours, and acidified with 2 N hydrochloric acid. The acidic mixture was extracted with diethyl ether and the organic phase extracted with 1 N sodium hydroxide . The combined basic extracts were acidified with 2 N hydrochloric acid, and extracted with diethyl ether. The extract was dried over anhydrous sodium sulfate, filtered and concentrated. The residue was recrystallized from diethyl ether to afford 0.450 g of the title compound as white crystals, 193° C. (dec.)

$^1$H NMR (DMSO-d$_6$, 400 MHz): δ 12.31 (s, 1H), 7.35 (dd, 1H), 7.17–7.13 (m, 2H), 7.07 (dt,1H), 6.91 (dd, 1H), 6.85 (t, 2H), 6.75 (d, 1H), 6.08 (d, 1H), 5.92 (br, 2H), 5.43 (m, 1H), 5.14 (br, 2H), 2.11 (s, 3H), 2.10–2.05 (m, 4H), 1.67–1.55 (m, 4H). Anal. Calcd. for C$_{27}$H$_{26}$N$_2$O$_3$: C 76.03, H 6.14, N 6.57. Found: C 75.71, H 6.16, N 6.48. MS [(−)-ESI, m/z]: 425.2 [M−H]$^−$. Calcd. for C$_{27}$H$_{25}$N$_2$O$_3$: 425.1862.

Step F. 10-[4-(1-Cyclohex-1-en-1-yl)-3-methylbenzoyl]-N-(2-pyridinylmethyl)-10,11-dihydro-5H-pyrrolo[2,1-c][1,4]benzodiazepine-3-carboxamide Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with [2-pyridinyl)methyl]amine in the manner of Example 3, Step D. HRMS [(+)-ESI, m/z]: 517.25972 [M+H]$^+$. Calcd. for $C_{33}H_{33}N_4O_2$: 517.25981

EXAMPLE 6

10-[4-(1-Cyclohex-1-en-1-yl)-3-methylbenzoyl]-N-(3-pyridinylmethyl)-10,11-dihydro-5H-pyrrolo[2,1-c][1,4]benzodiazepine-3-carboxamide Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with [(3-pyridinyl)methyl]amine in the manner of Example 3, Step D. HRMS [(+)-ESI, m/z]: 517.25943 [M+H]$^+$. Calcd. for $C_{33}H_{33}N_4O_2$: 517.25981

EXAMPLE 7

10-[4-(1-Cyclohex-1-en-1-yl)-3-methylbenzoyl]-N-[2-(2-pyridinyl)ethyl]-10,11-dihydro-5H-pyrrolo[2,1-c][1,4]benzodiazepine-3-carboxamide Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with [(2-pyridinyl)ethyl]amine in the manner of Example 3, Step D. HRMS [(+)-ESI, m/z]: 531.27522 [M+H]$^+$. Calcd. for $C_{34}H_{35}N_4O_2$: 531.27546.

EXAMPLE 8

10-[4-(1-Cyclohex-1-en-1-yl)-3-methylbenzoyl]-N-methyl-N-[2-(2-pyridinyl)ethyl]-10,11-dihydro-5H-pyrrolo[2,1-c][1,4]benzodiazepine-3-carboxamide Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with N-methyl-N-[2-(2-pyridinyl)ethyl]amine in the manner of Example 3, Step D. HRMS [(+)-ESI, m/z]: 545.29048 [M+H]$^+$. Calcd. for $C_{35}H_{37}N_4O_2$: 545.29111

EXAMPLE 9

{10-[4-(1-Cyclohex-1-en-1-yl)-3-methylbenzoyl]-10,11-dihydro-5H-pyrrolo[2,1-c][1,4]benzodiazepin-3-yl}[4-(2-pyridinyl)-1-piperazinyl]methanone Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with 4-(2-pyridinyl)-1-piperazine in the manner of Example 3, Step D. HRMS [(+)-ESI, m/z]: 572.30182 [M+H]$^+$. Calcd. for $C_{36}H_{38}N_5O_2$: 572.30201.

EXAMPLE 10

10-[4-(1-Cyclohex-1-en-1-yl)-3-methylbenzoyl]-N-(4-pyridinylmethyl)-10,11-dihydro-5H-pyrrolo[2,1-c][1,4]benzodiazepine-3-carboxamide Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with [(4-pyridinyl)methyl]amine in the manner of Example 3, Step D. HRMS [(+)-ESI, m/z]: 517.25954 [M+H]$^+$. Calcd. for $C_{33}H_{33}N_4O_2$: 517.25981.

EXAMPLES 11

10-[4-(1-Cyclohex-1-en-1-yl)-3-methylbenzoyl]-N-methyl-N-(3-pyridinylmethyl)-10,11-dihydro-5H-pyrrolo[2,1-c][1,4]benzodiazepine-3-carboxamide Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with N-methyl-N-[(3-pyridinyl)methyl]amine in the manner of Example 3, Step D. HRMS [(+)-ESI, m/z]: 531.27554 [M+H]$^+$. Calcd. for $C_{34}H_{35}N_4O_2$: 531.27546.

EXAMPLE 12

{10-[4-(1-Cyclohex-1-en-1-yl)-3-methylbenzoyl]-10,11-dihydro-5H-pyrrolo[2,1--c][1,4]benzodiazepin-3-yl}[4-(4-pyridinyl)-1-piperazinyl]methanone Prepared by acylation of 10-(4-cyclohex-1-en-1-yl-3-methyl-benzoyl)-10,11-dihydro-5H-pyrrolo [2,1-c][1,4] benzodiazepine-3-carboxylic acid of Example 5, Step E with 4-(4-pyridinyl)-1-piperazine in the manner of Example 3, Step D. HRMS [(+)-ESI, m/z]: 572.30113 [M+H]$^+$. Calcd. for $C_{36}H_{38}N_5O_2$: 572.30201.

EXAMPLE 13

10-[4-(1-Cyclohex-1-en-1-yl)-3-methylbenzoyl]-N-methyl-N-[2-(4-pyridinyl)ethyl]-10,11-dihydro-5H-pyrrolo[2,1-c][1,4]benzodiazepine-3-carboxamide Prepared by acylation of 10-(4-cyclohex-1-enyl-3-methyl-benzoyl)-10,11-dihydro-5H-pyrrolo [2,1-c][1,4] benzodiazepine-3-carboxylic acid of Example 5, Step E with N-methyl N-[2-(4-pyridinyl)ethyl]amine in the manner of Example 3, Step D. HRMS [(+)-ESI, m/z]: 545.29081 [M+H]$^+$. Calcd. for $C_{35}H_{37}N_4O_2$: 545.29111

What is claimed:

1. A compound of formula (I):

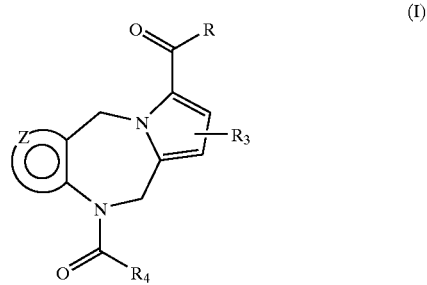

wherein

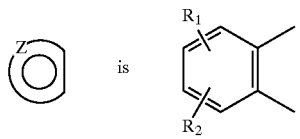 is $R_1$ and $R_2$ are, independently, selected from hydrogen, ($C_1$–$C_6$)lower alkyl, halogen, cyano, trifluoromethyl, hydroxy, amino, (C₁–C₆) lower alkylamino, (C₁–C₆) lower alkoxy, —OCF₃, (C₁–C₆) lower alkoxycarbonyl, —NHCO[(C₁–C₆)lower alkyl], carboxy, —CONH₂, —CONH (C₁–C₆) lower alkyl, or —CON[(C₁–C₆) lower alkyl]₂;

R₃ is a substituent selected from hydrogen, (C₁–C₆) lower alkyl, (C₁–C₆) lower alkoxy, hydroxy, amino, (C₁–C₆) lower alkylamino, —CO(C₁–C₆) lower alkyl, or halogen;

R₄ consists of the moiety B-C;

wherein B is selected from the group of:

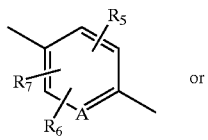

(a)

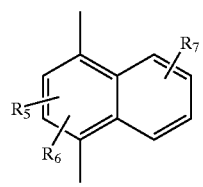

(b)

and C is defined as:

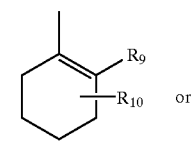

(c)

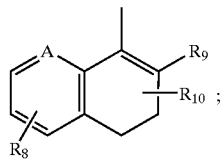

(d)

wherein:

A is CH;

R₅, R₆, R₇ and R₈ are independently, selected from hydrogen, (C₁–C₆) lower alkyl, (C₁–C₆) lower alkoxy, hydroxy(C₁–C₆ alkyl)—, alkoxy(C₁–C₆ alkyl)—, acyloxy (C₁–C₆ alkyl)—, (C₁–C₆) lower alkylcarbonyl, (C₃–C₆) lower alkenyl, (C₃–C₆) lower alkynyl, (C₃–C₈) cycloalkyl, formyl, cycloalkylcarbonyl, carboxy, alkoxycarbonyl, cycloalkyloxycarbonyl, aryl alkyloxycarbonyl, carbamoyl, —O—CH₂—CH=CH₂, halogen, halo lower alkyl, trifluoromethyl, —OCF₃, —S(lower alkyl), —OC(O)N[lower alkyl]₂, —CONH (lower alkyl), —CON[lower alkyl]₂, lower alkylamino, di-lower alkylamino, lower alkyl di-lower alkylamino, hydroxy, cyano, trifluoromethylthio, nitro, amino, lower alkylsulfonyl, aminosulfonyl, lower alkylaminosulfonyl,

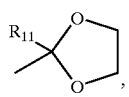

phenyl or naphthyl;

R₉ is chosen from the group of hydrogen, lower alkyl, hydroxy(C₁–C₆ alkyl)—, alkoxy(C₁–C₆ alkyl)—, -acyloxy (C₁–C₆ alkyl)—, alkoxycarbonyl, —CON

[(C₁–C₆) lower alkyl]₂, cyano; or aryl, optionally substituted by halogen, or lower alkoxy;

R₁₀ represents one to two substituents chosen independently, from the group of hydrogen, lower alkyl, hydroxy(C₁–C₆ alkyl)—, alkoxy(C₁–C₆alkyl)—, acyloxy(C₁–C₆ alkyl)—, [(C₁–C₆) lower alkyl]₂, carbonyl,

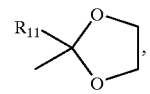

azido, amino, —NH[lower alkyl], —N[lower alkyl]₂, amino carbonyl lower alkyl, phthalimido, cyano, halogen, thio lower alkyl, aryloxy, arylthio, aryl optionally substituted with one to three substituents chosen from (C₁–C₆) lower alkyl, alkoxy or halogen; hydroxy, lower alkoxy, —OSO₂R₁₇, or OP' wherein P' is tert-butyl dimethylsilyl, tert-butyl diphenylsilyl, carbonyl loweralkyl, carbonyl trifluoro lower alkyl, aryl lower alkyl, arylcarbonyl, methoxymethyl, or methylthiomethyl; with the proviso that when R₁₀ represents two substituents, the two substituents may be joined together to form with the cyclohexene ring to which they are attached a bicyclic system;

R₁₁, is selected from the group of hydrogen, or (C₁–C₆) lower alkyl; and

R is selected from any of the following groups:

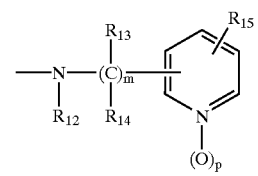

(h)

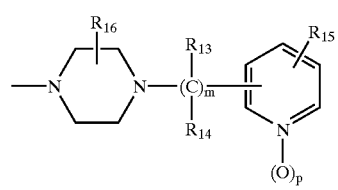

(i)

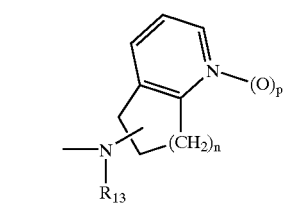

(j)

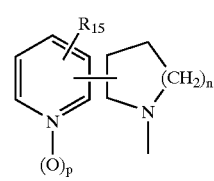

(k)

wherein:
$R_{12}$ is selected from the group of hydrogen, $(C_1-C_6)$ lower alkyl, cyanoethyl or

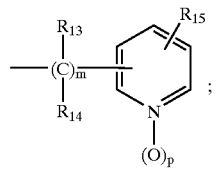

$R_{13}$ and $R_{14}$ are, independently, selected from the group of hydrogen or $(C_1-C_6)$ lower alkyl;
$R_{15}$ is one or two substituents selected, independently, from the group of hydrogen, $(C_1-C_6)$ lower alkyl, halogen, trifluoromethyl, $(C_1-C_6)$ lower alkoxy, $(C_1-C_6)$ lower alkoxycarbonyl,

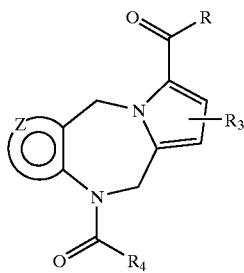

or
$R_{16}$ represents one to two substituents selected, independently, from hydrogen, or $(C_1-C_6)$ lower alkyl;
$R_{17}$ is selected from the group of hydrogen, $(C_1-C_6)$ lower alkyl, trifluoro lower alkyl, or aryl optionally substituted by lower alkyl;
m is an integer from 0 to 2;
n is an integer from 1 to 2;
and p is an integer from 0 to 1;
or the pharmaceutically acceptable salts thereof.

2. A compound of claim 1 of the formula:

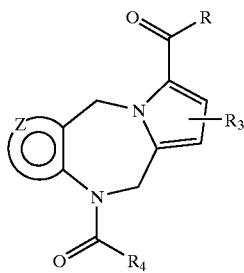

where:

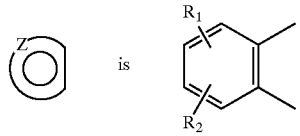

$R_1$ and $R_2$ are, independently, selected from hydrogen, $(C_1-C_6)$ lower alkyl, halogen, cyano, trifluoromethyl, hydroxy, amino, $(C_1-C_6)$ lower alkylamino, $(C_1-C_6)$ lower alkoxy, —OCF$_3$, $(C_1-C_6)$ lower alkoxycarbonyl, —NHCO[$(C_1-C_6)$lower alkyl], carboxy, —CONH$_2$, —CONH $(C_1-C_6)$ lower alkyl, or —CON[$(C_1-C_6)$ lower alkyl]$_2$;
$R_3$ is a substituent selected from hydrogen, $(C_1-C_6)$ lower alkyl, $(C_1-C_6)$ lower alkoxy, hydroxy, amino, $(C_1-C_6)$ lower alkylamino, —CO($C_1-C_6$) lower alkyl, or halogen;
$R_4$ consists of the moiety B-C;

wherein B is selected from the group of:

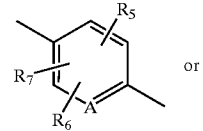

(a)

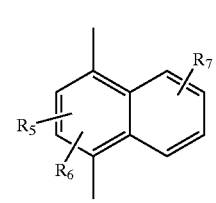

(b)

and C is defined as:

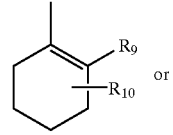

(c)

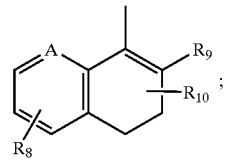

(d)

wherein:
A is CH;
$R_5$, $R_6$, $R_7$ and $R_8$ are independently, selected from H, $(C_1-C_6)$ lower alkyl, $(C_1-C_6)$ lower alkoxy, hydroxy $(C_1-C_6$ alkyl)—, alkoxy$(C_1-C_6$ alkyl)—, acyloxy$(C_1-C_6$ alkyl)—, $(C_1-C_6)$ lower alkylcarbonyl, $(C_3-C_6)$ lower alkenyl, $(C_3-C_6)$ lower alkynyl, $(C_3-C_8)$ cycloalkyl, formyl, cycloalkylcarbonyl, carboxy, alkoxycarbonyl, cycloalkyloxycarbonyl, carbamoyl, —O—CH$_2$—CH=CH$_2$, halogen, halo lower alkyl, trifluoromethyl, —OCF$_3$, —S(lower alkyl), —OC(O)N[lower alkyl]$_2$, —CONH(lower alkyl), —CON[lower alkyl]$_2$, lower alkylamino, di-lower alkylamino, lower alkyl di-lower alkylamino, hydroxy, cyano, trifluoromethylthio, nitro, amino, lower alkylsulfonyl, aminosulfonyl, or lower alkylaminosulfonyl;
$R_9$ is chosen from the group of hydrogen, lower alkyl, hydroxy$(C_1-C_6$ alkyl)—, alkoxy$(C_1-C_6$ alkyl)—, acyloxy$(C_1-C_6$ alkyl)—, alkoxycarbonyl, —CON[$(C_1-C_6)$ lower alkyl]$_2$, or cyano;
$R_{10}$ represents one to two substituents chosen independently, from the group of hydrogen, lower alkyl, hydroxy$(C_1-C_6$ alkyl)—, alkoxy$(C_1-C_6)$alkyl—, acyloxy$(C_1-C_6)$—, [$(C_1-C_6)$ lower alkyl]$_2$, carbonyl, azido, amino, —NH [lower alkyl], —N[lower alkyl]$_2$, amino carbonyl lower alkyl, phthalimido, cyano, halogen, thio lower alkyl, aryloxy, arylthio, hydroxy, lower alkoxy, —OSO$_2$R$_{17}$, or OP' wherein P' is tert-butyl dimethylsilyl, tert-butyl diphenylsilyl, carbonyl loweralkyl, carbonyl trifluoro lower alkyl, methoxymethyl, or methylthiomethyl;
$R_{11}$ is selected from the group of hydrogen, or $(C_1-C_6)$ lower alkyl; and R is selected from any of the following groups:

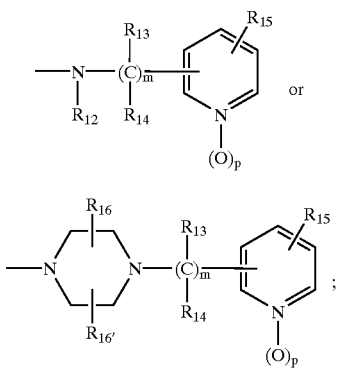

wherein:
$R_{12}$ is selected from the group of hydrogen, $(C_1–C_6)$ lower alkyl, or cyanoethyl;
$R_{13}$ and $R_{14}$ are, independently, selected from H or $(C_1–C_6)$ lower alkyl;
$R_{15}$ is one or two substituents selected, independently, from the group of hydrogen, $(C_1–C_6)$ lower alkyl, halogen, trifluoromethyl, $C_1–C_6$ lower alkoxy, $(C_1–C_6)$ lower alkoxycarbonyl;
$R_{16}$ and $R_{16'}$ are selected independently from H, or $(C_1–C_6)$ lower alkyl;
m is an integer from 0 to 2;
and p is an integer from 0 to 1;
or a pharmaceutically acceptable salt thereof.

3. A compound of claim 1 which is selected from the group of
(a) 10-(5-Chloro-4-cyclohex-1-en-1-yl-2-methoxybenzoyl)-N-methyl-N-(pyridin-3-ylmethyl)-10,11-dihydro-5H-pyrrolo [2,1-c][1,4]benzodiazepine-3-carboxamide;
(b) 10-[4-((3R)-3-Hydroxy-2-methyl-cyclohex-1-en-1-yl)-3-methyl-benzoyl]-10,11-dihydro-5H-pyrrolo[2,1-c][1,4]benzodiazepine-3-carboxylic acid methyl-pyridin-3-yl methyl-amide; or
(c) 10-[4-(1-Cyclohex-1-en-1-yl)-3-methylbenzoyl]-N-(2-pyridinylmethyl)-10,11-dihydro-5H-pyrrolo[2,1-c][1,4]benzodiazepine-3-carboxamide;
or a pharmaceutically acceptable salt thereof.

4. A compound of claim 1 which is selected from the group of:
(a) 10-[4-(1-Cyclohex-1-en-1-yl)-3-methylbenzoyl]-N-(3-pyridinylmethyl)-10,11-dihydro-5H-pyrrolo[2,1-c][1,4]benzodiazepine-3-carboxamide;
(b) 10-[4-(1-Cyclohex-1-en-1-yl)-3-methylbenzoyl]-N-[2-(2-pyridinyl)ethyl]-10,11-dihydro-5H-pyrrolo[2,1-c][1,4]benzodiazepine-3-carboxamide;
(c) 10-[4-(1-Cyclohex-1-en-1-yl)-3-methylbenzoyl]-N-methyl-N-[2-(2-pyridinyl)ethyl]-10,11-dihydro-5H-pyrrolo[2,1-c][1,4]benzodiazepine-3-carboxamide; or
(d) {10-[4-(1-Cyclohex-1-en-1-yl)-3-methylbenzoyl]-10,11-dihydro-5H-pyrrolo[2,1-c][1,4]benzodiazepin-3-yl}[4-(2-pyridinyl)-1-piperazinyl]methanone; or a pharmaceutically acceptable salt thereof.

5. A compound of claim 1 which is selected from the group of:
(a) 10-[4-(1-Cyclohex-1-en-1-yl)-3-methylbenzoyl]-N-(4-pyridinylmethyl)-10,11-dihydro-5H-pyrrolo[2,1-c][1,4]benzodiazepine-3-carboxamide;
(b) 10-[4-(1-Cyclohex-1-en-1-yl)-3-methylbenzoyl]-N-methyl-N-(3-pyridinylmethyl)- 10,11-dihydro-5H-pyrrolo[2,1-c][1,4]benzodiazepine-3-carboxamide;
(c) {10-[4-(1-Cyclohex-1-en-1yl)-3-methylbenzoyl]-10,11-dihydro-5H-pyrrolo[2,1-c][1,4]benzodiazepin-3-yl}[4-(4-pyridinyl)-1-piperazinyl]methanone; or
(d) 10-[4-(1-Cyclohex-1-en-1-yl)-3-methylbenzoyl]-N-methyl-N-[2-(4-pyridinyl)ethyl]-10,11-dihydro-5H-pyrrolo[2,1-c][1,4]benzodiazepine-3-carboxamide; or a pharmaceutically acceptable salt form thereof.

6. A pharmaceutical composition comprising a pharmaceutically effective amount of a compound of claim 1 and a pharmaceutically acceptable carrier or excipient.

7. A compound of claim 1 that is
(a) 10-(5-Chloro-4-cyclohex-1-en-1-yl-2-methoxybenzoyl)-N-methyl-N-(pyridin-3-ylmethyl)-10,11-dihydro-5H-pyrrolo [2,1-c][1,4]benzodiazepine-3-carboxamide L-(+)-tartaric acid salt hemihydrate; or
(b) 10-[4-((3R)-3-Hydroxy-2-methyl-cyclohex-1-en-1-yl)-3-methyl-benzoyl]-10,11-dihydro-5H-pyrrolo[2,1-c][1,4]benzodiazepine-3-carboxylic acid methyl-pyridin-3-yl methyl-amide L-(+)-tartaric acid salt.

8. A method comprising contacting an oxytocin receptor with a compound of claim 1 or a pharmaceutically acceptable salt form thereof.

9. A method of antagonizing the oxytocin receptor in a mammal comprising providing to the mammal an effective amount of a compound of claim 1.

10. A method comprising contacting a vasopressin receptor with a compound of claim 1.

11. A method for inhibiting pre-term labor in a mammal comprising administering to a mammal in need thereof a pharmaceutically effective amount of a compound of claim 1, or a pharmaceutically acceptable salt form thereof.

12. A method for suppressing labor prior to caesarean delivery in a mammal comprising administering to a mammal in need thereof a pharmaceutically effective amount of a compound of claim 1, or a pharmaceutically acceptable salt form thereof.

13. A method for inhibiting dysmenorrhea in a mammal comprising administering to a mammal in need thereof a pharmaceutically effective amount of a compound of claim 1, or a pharmaceutically acceptable salt form thereof.

14. A method for inhibiting endometritis in a mammal comprising administering to a mammal in need thereof a pharmaceutically effective amount of a compound of claim 1, or a pharmaceutically acceptable salt form thereof.

15. A method of antagonizing the vasopressin receptor in a mammal comprising providing to the mammal an effective amount of a compound of claim 1.

* * * * *